(12) United States Patent
Von Schuckmann

(10) Patent No.: US 8,434,476 B2
(45) Date of Patent: May 7, 2013

(54) DISPENSER FOR PULVERULENT SUBSTANCES

(76) Inventor: Alfred Von Schuckmann, Kevelaer (DE)

( * ) Notice: Subject to any disclaimer, the term of this patent is extended or adjusted under 35 U.S.C. 154(b) by 1077 days.

(21) Appl. No.: 12/442,721

(22) PCT Filed: Jul. 18, 2007

(86) PCT No.: PCT/EP2007/057409
§ 371 (c)(1),
(2), (4) Date: Mar. 25, 2009

(87) PCT Pub. No.: WO2008/037519
PCT Pub. Date: Apr. 3, 2008

(65) Prior Publication Data
US 2010/0083962 A1    Apr. 8, 2010

(30) Foreign Application Priority Data
Sep. 26, 2006    (DE) .......................... 10 2006 045 788

(51) Int. Cl.
*A61M 15/00* (2006.01)
*A61M 16/00* (2006.01)

(52) U.S. Cl.
USPC ............ 128/203.21; 128/200.24; 128/203.15; 128/205.23

(58) Field of Classification Search ............. 128/200.24, 128/203.15, 203.21, 205.23
See application file for complete search history.

(56) References Cited

U.S. PATENT DOCUMENTS

| 4,627,432 A | 12/1986 | Newell et al. |
| 4,778,054 A * | 10/1988 | Newell et al. .................. 206/531 |
| 4,811,731 A | 3/1989 | Newell et al. |
| 5,035,237 A | 7/1991 | Newell et al. |
| 5,875,776 A * | 3/1999 | Vaghefi .................... 128/203.15 |
| 6,561,186 B2 * | 5/2003 | Casper et al. ............. 128/203.15 |
| 7,219,665 B1 * | 5/2007 | Braithwaite ............. 128/203.21 |
| 7,451,761 B2 * | 11/2008 | Hickey et al. ............ 128/203.21 |
| 2002/0078951 A1 * | 6/2002 | Nichols et al. ........... 128/200.22 |
| 2005/0048003 A1 * | 3/2005 | Ohki et al. ..................... 424/46 |
| 2007/0151562 A1 * | 7/2007 | Jones et al. .............. 128/203.21 |

FOREIGN PATENT DOCUMENTS

| EP | 0211595 B1 | 11/1991 |
| GB | 2129691 A | 5/1984 |

* cited by examiner

*Primary Examiner* — Lynne Anderson
*Assistant Examiner* — Bradley Philips
(74) *Attorney, Agent, or Firm* — Laurence A. Greenberg; Werner H. Stemer; Ralph E. Locher

(57) ABSTRACT

The invention relates to a dispenser (1) for pulverulent substances (30), in particular medicaments, from a blister pack (25), dome-shaped cavities (26) of which that are disposed on a base layer (28) can, by movement in a dispenser housing (4), be brought step by step into an emptying position, in which they can be opened by means of a needle (31) and can be emptied by a suction air stream (a) leading to a mouthpiece (6). To achieve optimum emptying of the cavities, it is proposed that the needle (31) passes crosswise through both lateral walls of the dome (29) of the cavities (preferably parallel to the base layer 28) in order to form a through path to the mouthpiece for suction air.

63 Claims, 19 Drawing Sheets

DISPENSER FOR PULVERULENT SUBSTANCES

BACKGROUND OF THE INVENTION

Field of the Invention

The invention relates to a dispenser for pulverulent substances, in particular medicaments, from a blister pack, done-shaped cavities of which can, by movement in a dispenser housing, be brought step by step into an emptying position, in which they can be opened by means of a needle and can be emptied by a suction air stream leading to a mouthpiece.

Dispensers of the type in question are known. They serve primarily for the inhalation of medicinal powdered substances, which furthermore are provided in apportioned manner in cavities of a blister pack. In this respect, reference is made for example to U.S. Pat. No. 4,778,054. The generic dispensers have, contained in a housing, a disk-shaped blister pack, which can be advanced step by step in the manner of a carousel and is provided with a plurality of dome-shaped cavities provided in a circular arrangement. Each cavity holds a portion of the pulverulent substance. The filled cavities are covered over by a laminated-on base layer, generally of aluminum foil. Each cavity brought into the emptying position is opened for inhalation by means of a needle, which pierces the dome wall and also the aluminum foil forming the base of the cavity. After retraction of the needle, the now opened cavity lies in a channel leading to the mouthpiece, for emptying by means of a suction air stream. Emptying presents problems, in particular specifically in dependence on the level of filling of the cavity. Handling is inconvenient.

With regard to the prior art described above, a technical problem addressed by the invention consists of improving a dispenser of the type in question, in particular with regard to the emptying of the individual cavities.

BRIEF SUMMARY OF THE INVENTION

This problem is solved first and foremost by the subject matter of claim 1, it being provided that the needle passes crosswise through the lateral wall of the dome and the two pierced holes, which are open after retraction of the needle, lie in the path of the suction air stream channel to the mouthpiece. Accordingly, for the emptying of a cavity, the dome is pierced twice by means of the needle. The aluminum foil, forming the base of the cavity, remains unaffected by this; it remains intact. By contrast, the previously known solutions envisage piercing of the aluminum foil, which can result in parts of the wall tearing away on account of the given material properties. These parts of the wall may come to lie in front of the other opening pierced in the dome, this having the effect of adversely affecting emptying of the cavity. In addition, uncontrolled tearing of the aluminum foil makes it possible for the pieces of foil at the edge of the opening to stand up into the dome space, possibly splaying to such a great extent that emptying may likewise be disturbed by the formation of pocket-like enclosures. These disadvantages are counteracted by the configuration according to the invention. The formation of the throughflow openings only in the dome, which is made from plastics, prevents detachment of parts of the wall during the course of the forming of the holes. In addition, as a result of the choice of material, holes formed in this way do not tear beyond the diameter of the needle, or not significantly beyond this diameter, which results in a correspondingly small degree of splaying of the edge of the opening and this also only in the direction of through-flow. A kind of pocket formation, in which pulverulent substance can become trapped during the course of emptying, is effectively prevented. A further advantage is obtained by both holes being disposed in the dome region. Breathing-in during the course of inhalation produces a suction air stream that passes through the dome, for example in the manner of a secant, and, by flowing through transversely and acting in a swirling and distributing manner under the dome, leads to complete emptying of the cavity.

Features are described hereafter that are of significance preferably in combination with the features of Claim 1 and/or Claims 2 and 3.

Thus, in a preferred configuration of the subject matter of the invention, it is provided that the needle passes through the dome wall in a straight line proceeding from the centre of the annular blister pack, this leading to the holes formed being aligned in projection. Accordingly, the suction air stream entraining the pulverulent substance is also made to pass through the dome in a substantially straight line, in the manner of a secant. In this respect, it is further preferred for the needle to pierce the dome on the diameter line, more preferably directly above the dome base formed by the aluminum foil, in which region the dome, which is thermoformed from a plastics material, has the greatest possible stability, this proving to be positive with regard to the punching of the holes and the resulting configuration of the edge of the holes. In addition, the holes formed in the dome assume the greatest possible distance from one another, which assists complete emptying as the suction air flows through.

The needle for piercing the dome has a diameter which leads to holes in the dome that allow a flow which is sufficient for emptying the dome. Thus, the needle has a diameter that is adapted to the diameter of the suction air stream channel, which does not necessarily mean that the diameter of the needle is equal to or only slightly smaller than the diameter of the channel. Rather, the diameter of the needle corresponds to approximately 15 to 80%-90%, preferably approximately 40 to 60%, of the diameter of the channel. In a further configuration, the diameter of the needle corresponds approximately to one sixth to one third of the diameter of the dome, this being, in the case of a preferred dome diameter, from 3 to 12 mm, more preferably from 4 to 10 mm. The dome is located preferably to fit in an accommodating hollow in a carrier.

The needle pierces the dome in the course of a manually actuated linear displacement of the needle. It is preferred in this respect that the needle passes through the dome while building up a spring force and that, after passing through the dome, the needle returns automatically, triggered by a release of the spring force, into a preferably stop-limited position, in which the spring force tends toward zero. This configuration proves to be of advantage, in particular when the triggering of the needle return displacement takes place automatically, i.e. without deliberate intervention by the user. To achieve a position ready for inhalation, all that the user has to do is to effect advance of the spring while building up the force of the spring. After the dome has been pierced, the built-up spring force is released automatically, for example with the automatic deactivation of a catch that restrains the spring during the course of the needle advance, this bringing about the return displacement of the needle under the load of the spring force as the needle leaves the dome. The release for the return displacement takes place more preferably immediately after piercing of the dome has been completed, i.e. immediately after the second hole has been punched in the dome. Alternatively, if not preferably, manual return displacement of the needle may also take place after piercing of the dome. However, the proposed self-triggering spring loading of the needle relieves the user of one operation.

In a preferred configuration of the subject matter of the invention, the needle is moved into the piercing position by means of a drag part. In the simplest way, this may be an arm which is articulated in the housing and by means of which a transmission is made possible. It is therefore further provided that the drag part can be displaced in a triggerable manner by way of an actuating element provided with an accessible handle. As a result of this configuration, the handle does not act directly on the needle, but rather, as preferred, indirectly via the also preferred actuating element that is secured to the handle in a rotationally fixed manner and via the drag part to be displaced by the actuating element. In a further configuration, this allows an indicated rotational handle displacement to be converted into a strictly linear displacement of the needle.

In the simplest way, the needle and the spring may be separate components. Furthermore, for example, a cylindrical spring disposed coaxially with the needle may therefore act on it. A leaf spring arrangement or spiral spring arrangement is also conceivable in this respect. However, a configuration is preferred in which the needle is formed in one piece with the spring, more preferably in such a way that the needle is produced as a solid component by the plastics injection-molding process, elastically yielding spring arms being molded-on at the end remote from the tip of the needle. In a preferred configuration, these extend on opposite sides of the end of the needle remote from the tip, furthermore as a segment of a circle in plan view up to an approximately semicircular shape, in order for the free ends to provide support on a housing wall, these free ends pointing in the direction of the tip of the needle. Other forms of spring formed in one piece with the needle are conceivable in this respect, also for example in the manner of straight spring arms which extend at an acute angle to the needle and also interact for example with in each case a sloping flank of the housing that displaces the spring arms into their tensile loading position.

The dispenser is designed for the delivery of apportioned pulverulent substances according to the number of cavities that are present in the blister pack. The dispenser is preferably designed in such a way that, once all the cavities have been emptied, the blister can be changed by the user without using any implement. After the emptying of a cavity, the blister pack is advanced by one step, preferably by means of a carrier, after which the next cavity arrives in the operative position. A stepping mechanism is provided for this purpose, moving the dome-shaped cavities step by step into the emptying position. This stepping mechanism can be manually actuated by the user. Accordingly, step-by-step movement of the cavities is deliberately brought about. Thus, it is provided in this respect for the stepping mechanism to interact with the actuating element that also serves for the displacement of the needle into the piercing position. In the simplest case, such a stepping mechanism comprises a switching finger and a restraining finger that secures the position reached, the fingers interacting with respectively associated latching recesses or the like. These are preferably formed in the carrier region that holds the blister pack. In an advantageous manner, the stepping mechanism is at least partially an integral part of the actuating element. The latter may be made for example in the form of a planar-form part with a molded-on handle, from which planar-form part the aforementioned switching finger is formed. In a preferred configuration, it is provided that, once the cavity has been emptied, the carrier accommodating the blister is advanced by one step during the course of a return displacement of the actuating element, this to be carried out manually. Thus, the actuating element is formed in such a way that, when there is a movement, more preferably a rotational movement, in one direction, it is configured for the advance of the needle to pierce the dome, while the succeeding return displacement of the actuating element serves for the step-by-step advance of the cavities, after which the actuating element arrives back in its starting position, from which the next needle actuation can take place. This position is also evident to the user from the handle that is fixed on the actuating element and is accessible from the outside.

A mouthpiece closure cap is also provided, to protect the mouthpiece that is otherwise open toward the interior of the housing from impurities. This closure cap is more preferably connected in a controlling manner to the annular blister carrier driven by the stepping mechanism; more preferably it can be displaced in dependence on the position of the blister carrier, in particular into the mouthpiece closing position. The closure cap is hinge-mounted on the dispenser housing, a blocking lug that is disposed in a rotationally fixed manner on the actuating element that controls the stepping mechanism also being provided. This blocking lug is arranged to interact with the mouthpiece closure cap, preferably in such a way that closing of the closure cap can only be achieved in the ready position for a next, intact cavity. For this purpose, the closure cap is provided at its rim with a recess, which is open at the edge and can be entered, in the ready position, by the blocking lug. At a spacing from the recess, the closure cap has a blocking shoulder, which interacts with the blocking lug in an unready position. This unready position is preferably the blister carrier position assumed immediately after inhalation, in which position an empty cavity correspondingly lies in the suction channel. If holes were possibly to be punched in the dome by means of the needle after this, on the assumption of finding a filled cavity, this would lead to possibly unnoticed improper inhalation. Thus, the safety feature that is brought about by means of the blocking lug is preferably arranged in such a way that, after opening of the closure cap from the mouthpiece-closed position, the dispenser is in a ready position, i.e. with an unopened cavity that has a portion to be inhaled in the flow channel.

It is very advantageous for the complete emptying of the cavities for the suction air stream emptying the cavity to be made to pass through the dispenser housing with a deflection of 180°, the emptying also taking place after the 180° deflection. In this case, the air is preferably sucked-in in the region of the mouthpiece, more preferably in the region of the mouthpiece attachment on the housing, thus also from the radial direction with reference to the general channel axis. After the 180° deflection in the housing, the suction air stream entrains the substance from the dome. Disposing the flow channel in this way achieves a short flow path, formed almost without further deflections, of the air transporting the substance to the mouthpiece. In the region of the dome, and also in a region in front of and behind the dome, the direction of flow is preferably arranged to be strictly linear. Before it leaves the mouthpiece, the suction air stream transporting the substance passes through a swirl chamber, in which an additional horizontal swirling is imparted to the suction air stream by providing tangentially entering secondary air openings, this leading to improved distribution of the coarser particles within the suction air.

The invention is explained in more detail below with reference to the accompanying drawings, which merely represent an exemplary embodiment and in which:

BRIEF DESCRIPTION OF THE SEVERAL
VIEWS OF THE DRAWING

DESCRIPTION OF THE INVENTION

Figure 1:
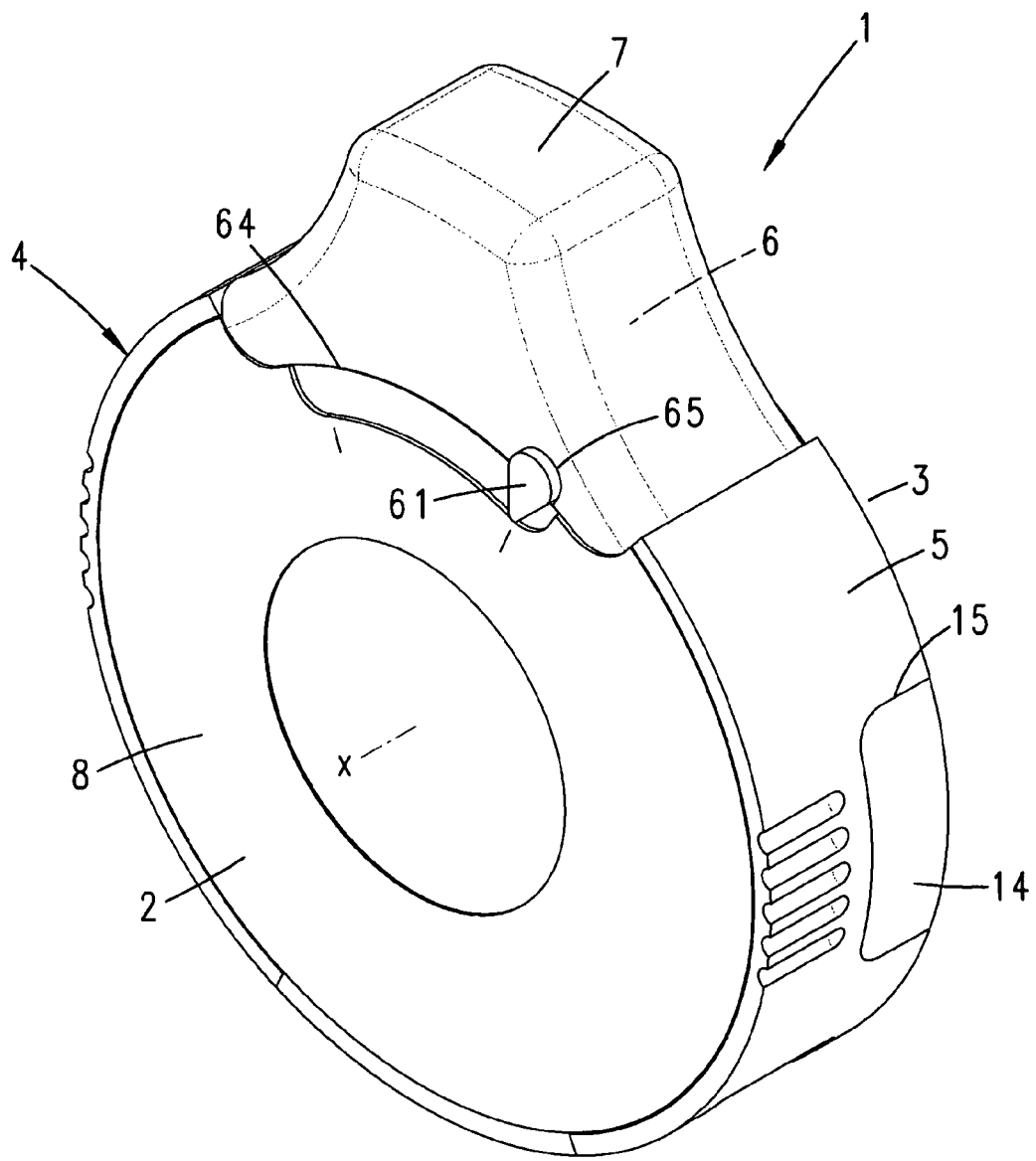
FIG. 1 shows the dispenser with mouthpiece closed, in perspective front view.
Figure 2:
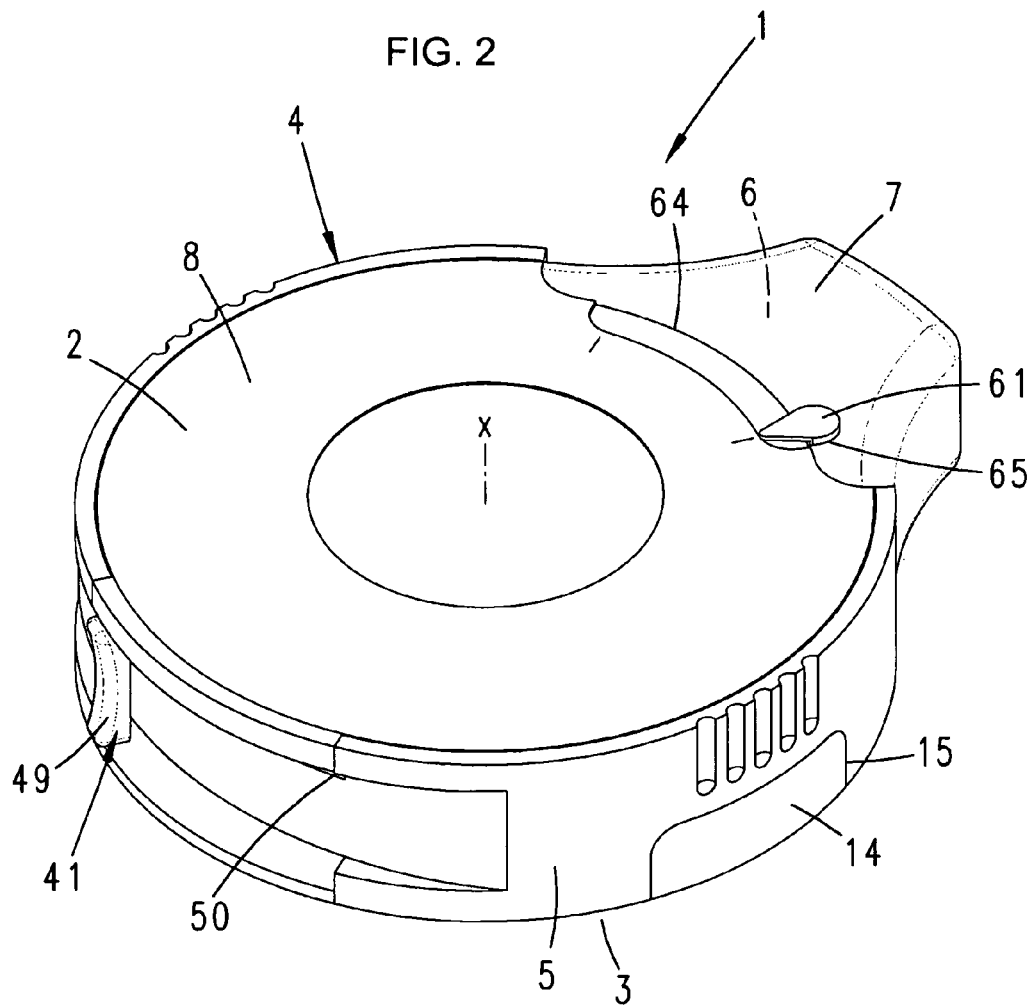
FIG. 2 shows a further perspective representation of the dispenser according to FIG. 1.
Figure 3:
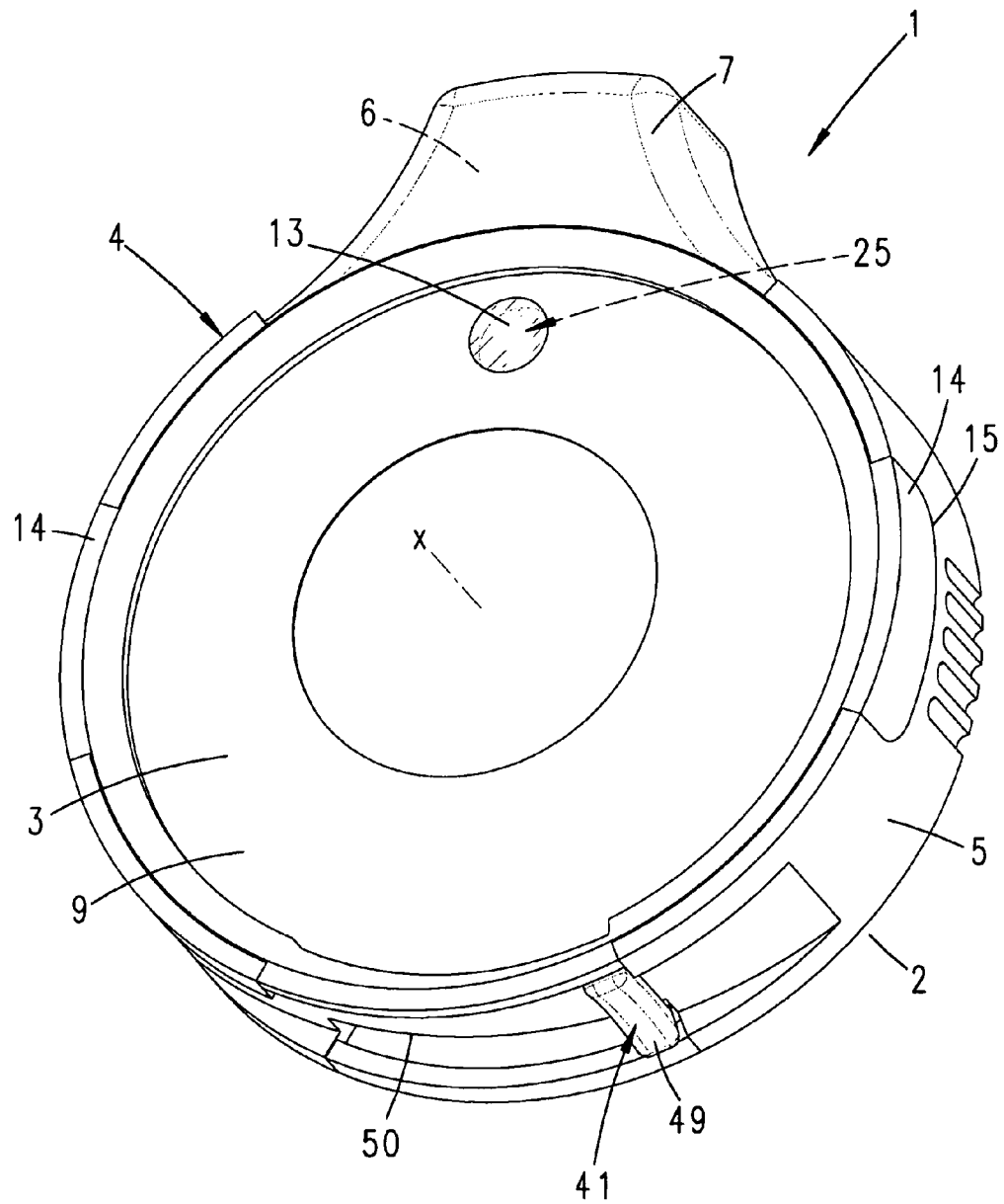
FIG. 3 shows the perspective rear view of this.
Figure 4:
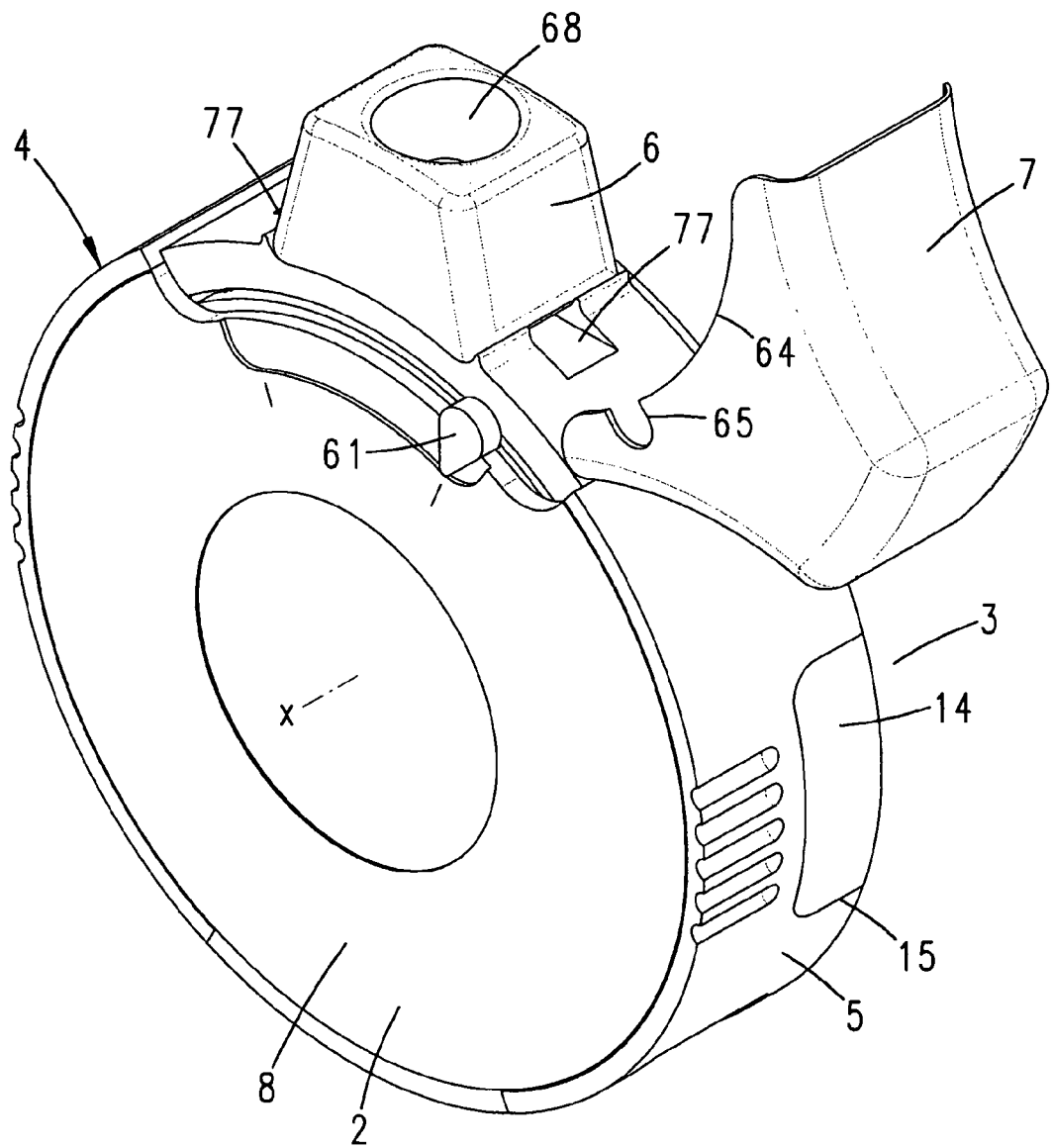
FIG. 4 shows a perspective representation corresponding to FIG. 1, but after pivoting the closure cap to expose the mouthpiece.
Figure 5:
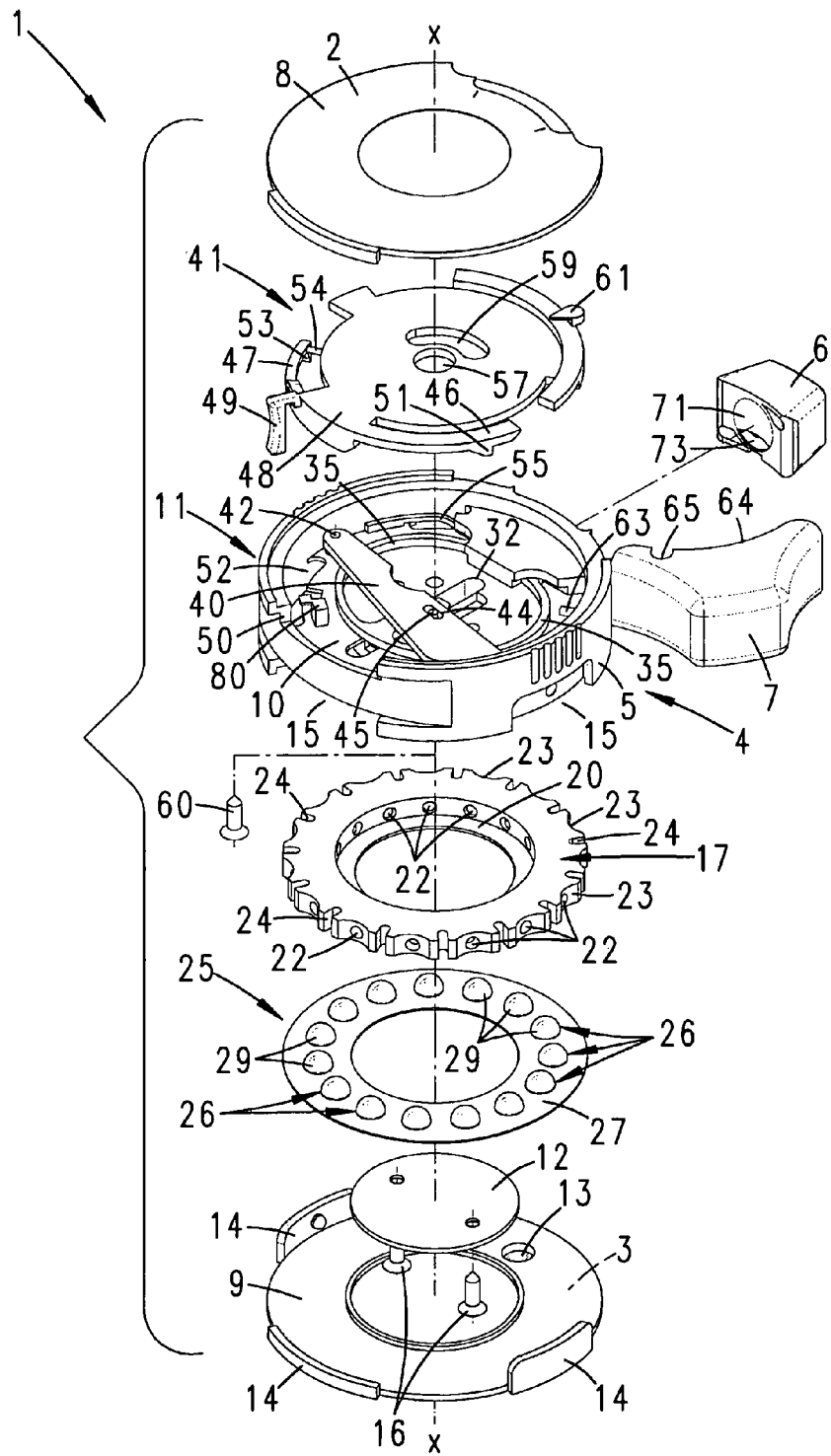
FIG. 5 shows a perspective exploded representation of the dispenser.
Figure 6:
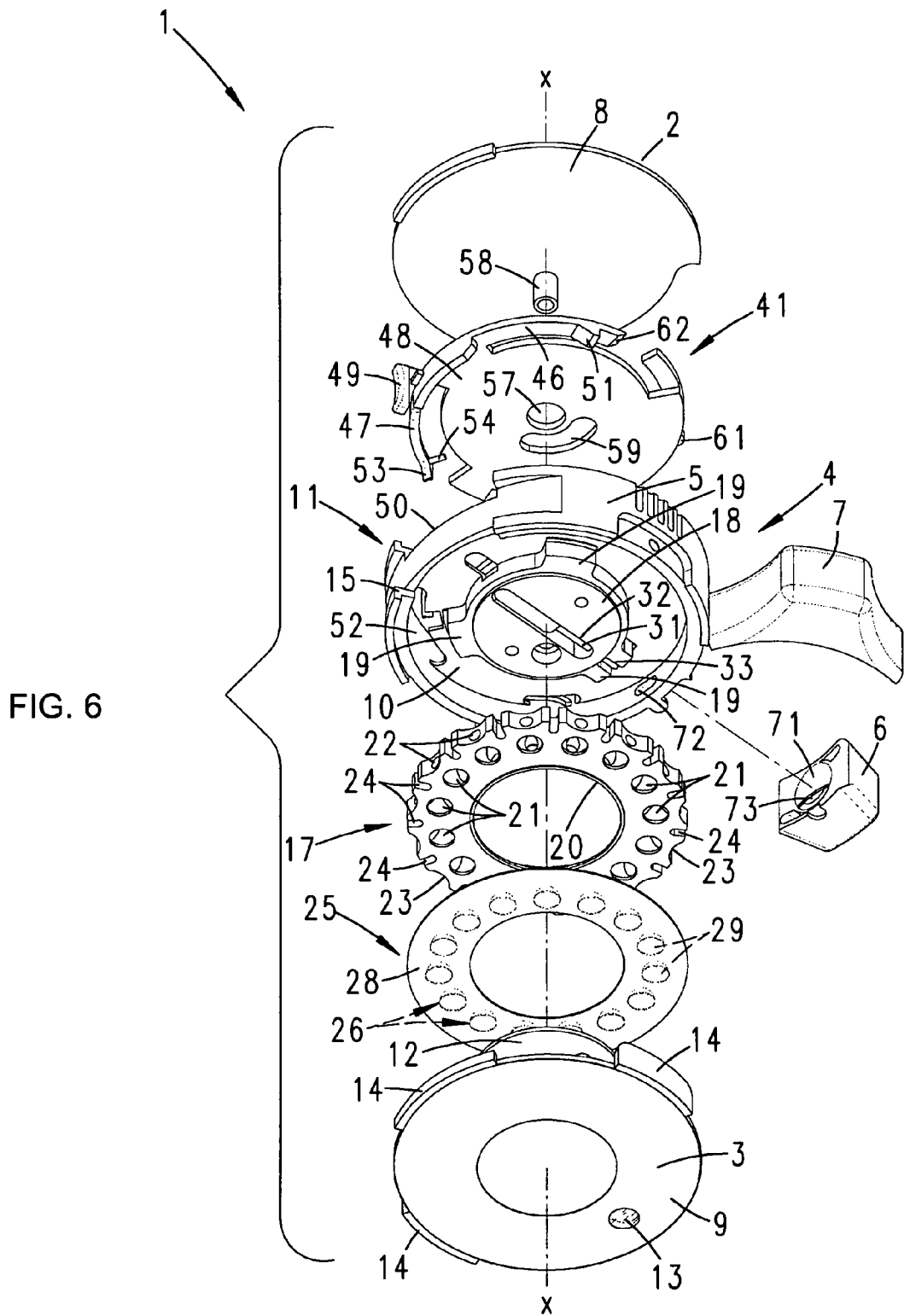
FIG. 6 shows a further exploded representation looking in the direction of undersides of the parts of the dispenser.
Figure 7:
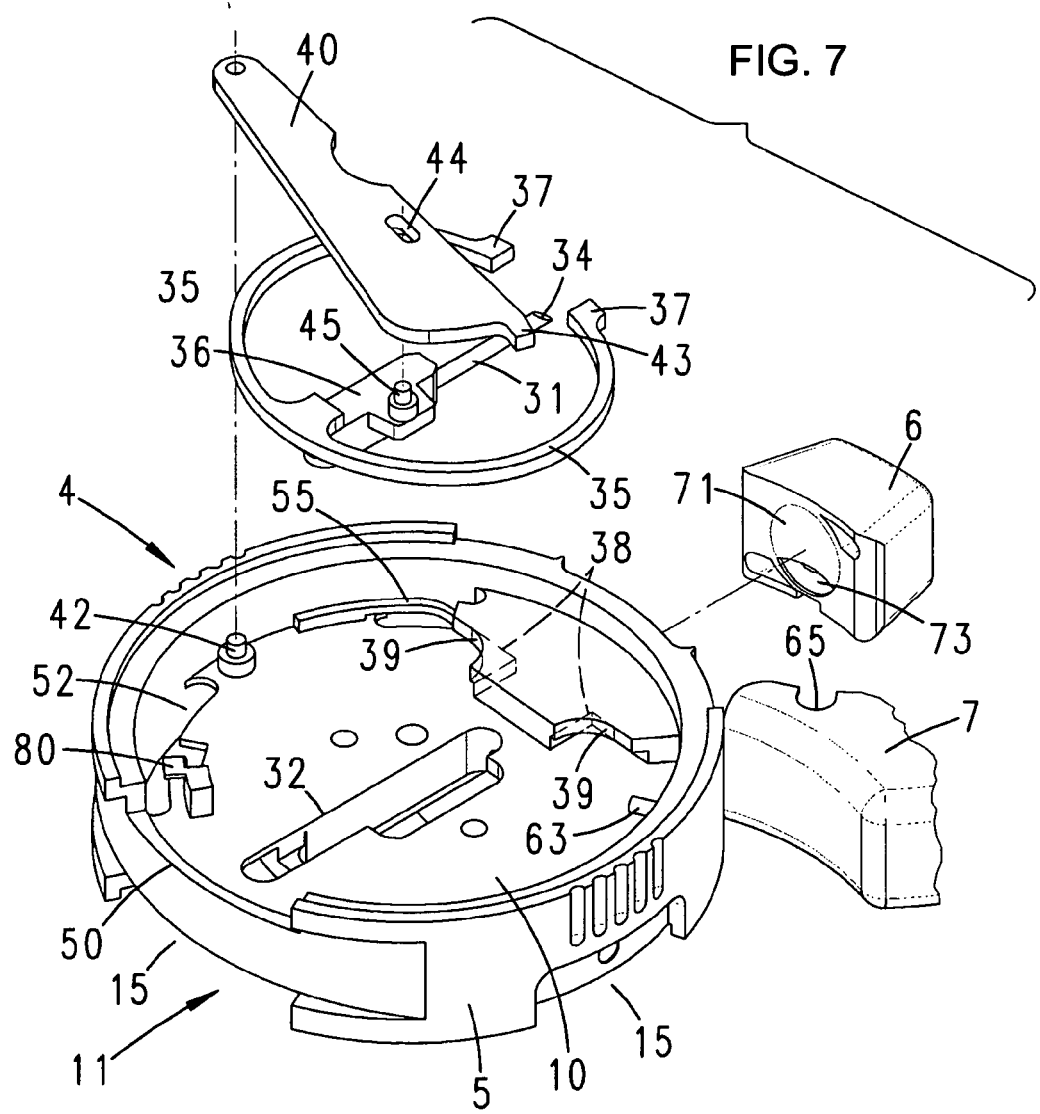
FIG. 7 shows a partial exploded representation of the basic housing of the dispenser, of the mouthpiece, and of a needle provided with a spring and a drag part.
Figure 8:
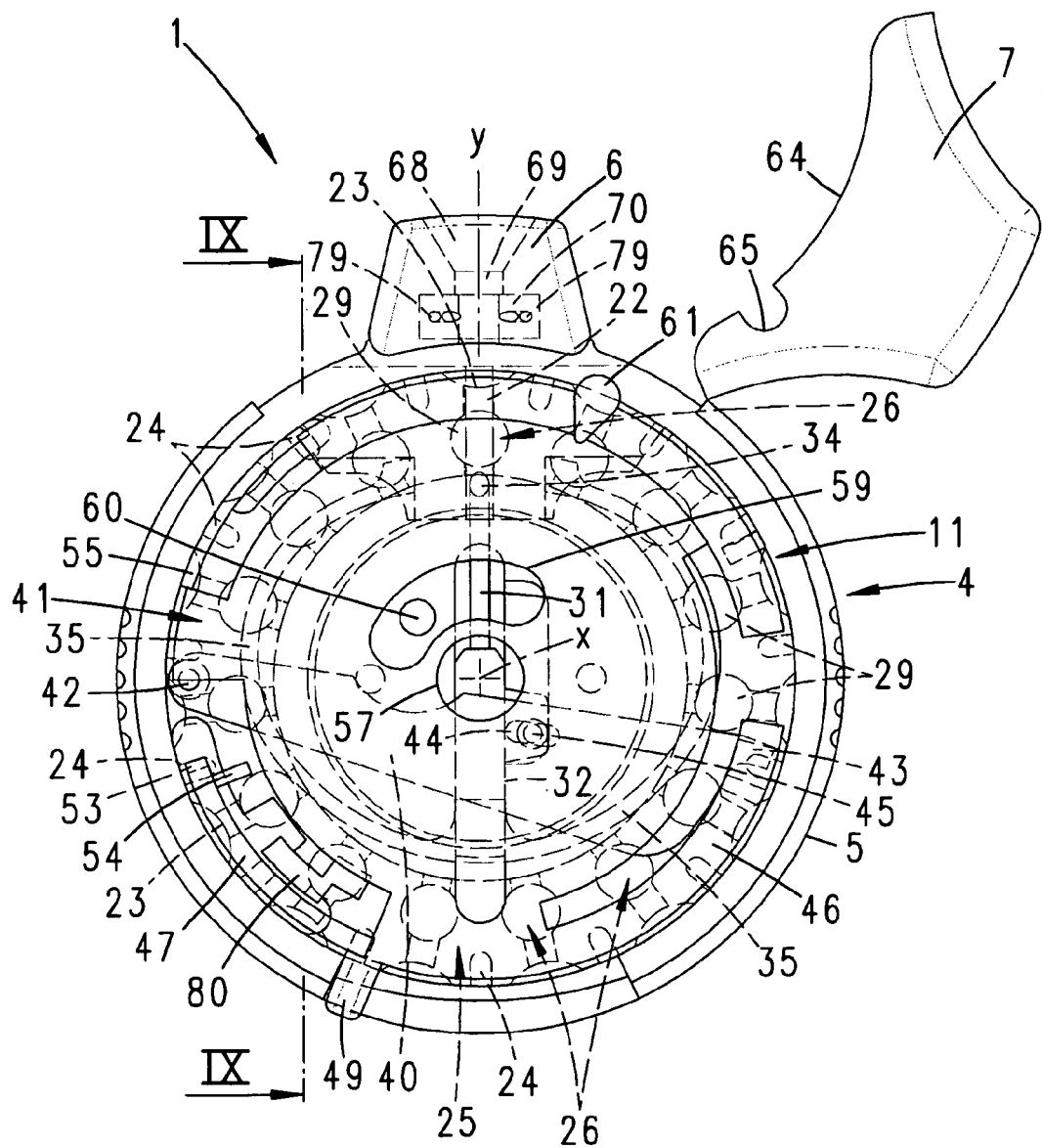
FIG. 8 shows a front view of the dispenser in the ready position, without a cover.
Figure 9:
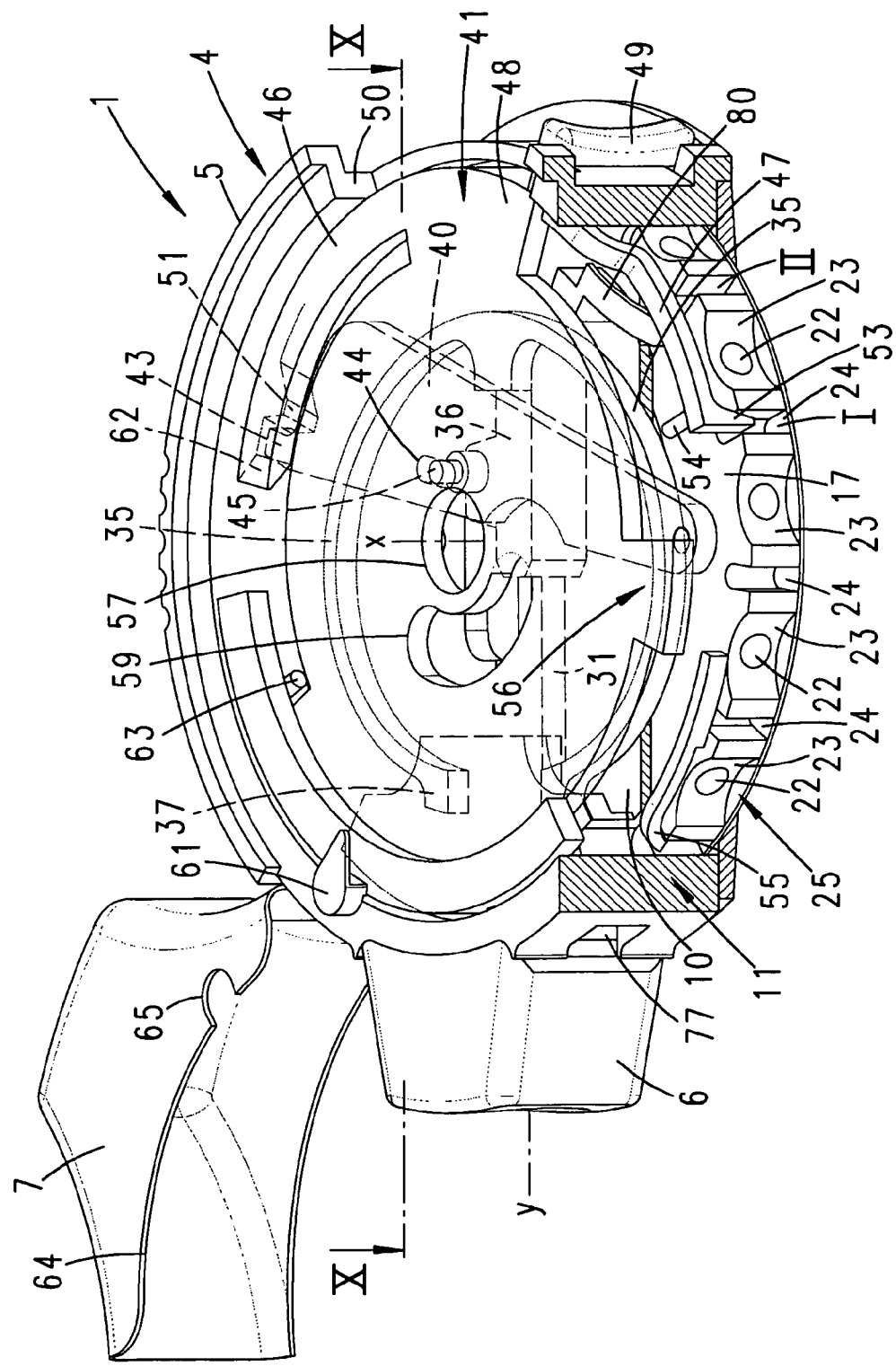
FIG. 9 shows the dispenser in a partially sectioned, perspective representation, likewise without the cover, in the ready position.

Shown and described in first instance with reference to FIGS. 1 to 4 is a dispenser 1 for pulverulent substances, in particular for the inhalation of suitable medicaments. With an overall handy format, the dispenser 1 is substantially circular in plan view, with a front side 2 in the form of a circular disk and a rear side 3 of the same configuration in plan view. These sides are spaced apart from each other in the axial direction and have a common dispenser axis x. The lateral wall 5, delimiting the dispenser housing 4 radially outwardly, extends along the facing peripheral edges of the front and rear sides, doing so with a thickness dimension in the axial direction that corresponds approximately to one third to one quarter of the diameter of the dispenser.

Extending radially outwardly from the overall approximately disk-shaped configuration of the housing 4, over about one eighth of the circumferential length, is a mouthpiece 6. This is used for effecting the inhalation by breathing in.

The mouthpiece 6 can be closed by a pivotable closure cap 7, which closure cap 7 is hinge-mounted on the lateral wall 5 of the housing 4. The hinge axis runs parallel to but offset from the housing axis x, so that the pivoting of the closure cap 7 takes place in the circumferential direction of the housing 4. The hinge mounting is selected in the form of a film hinge. This is formed in such a way that the closure cap 7, in the open position according to the representation in FIG. 4, goes into a self-holding state. In the closure position, represented for example in FIG. 1, the closure cap 7 is held in a latched position, so that opening of the same is only possible deliberately.

The housing 4 is substantially made up of a disk-shaped end wall 8, forming the front side 2, an end wall 9, provided with the same diameter and intended for forming the rear side 3, and the mentioned lateral wall 5, which is, in plan view, in the shape of a circular ring. Centrally in the direction of its thickness—seen in the direction of the x axis—the lateral wall is provided with an intermediate base 10. This is formed in one piece with the lateral wall 5.

The front end wall 8 and the housing middle part 11 with intermediate base 10 and lateral wall 5 are preferably no longer operationally separable from one another after assembly. On the other hand, the end wall 9, defining the rear side 3, is held on the housing middle part 11 in such a way that it can be removed to expose the covered space; thus, in particular, it is in latching engagement at its periphery.

The end wall 9 is also provided in a radially outer region with a transparent region to form a viewing window 13. When the end wall 9 is fixed on the housing middle part 11, said viewing window is positioned in such an orientation that it is associated with the mouthpiece 6. For it to be disposed positionally correctly on the housing middle part 11, the end wall 9 has lug-like engaging means 14, which engage in corresponding peripherally open recesses 15 in the lateral wall region 5 and do not allow any other positioning. The latching fixation is effected in these engaging regions.

When the dispenser 1 is formed as a whole from injection-molded plastics parts, the viewing window 13 may for example be formed during the course of a two-component injection-molding process, in which a transparent plastics is used in the region representing the viewing window 13. Depending on the design of the transparent area, the viewing window 13 may additionally create an effect similar to a magnifying glass.

The intermediate base 10 substantially divides the housing middle part 11 into a mechanism region, covered over by the operationally non-detachable end wall 8 and consequently protected, and a substance-carrier region associated with the detachable end wall 9. A carrier 17 in the form of a circular ring is accommodated in the latter region. This carrier has a thickness measured in the axial direction that is somewhat less than the clear height between the facing surface of the intermediate base 10 and the end wall 9 covering over this region.

The carrier 17 is guided radially inwardly in the circumferential direction about the x axis. For this purpose, the intermediate base 10 has firstly a central circular-cylindrical upstanding portion 18, from which there extend, seen over the circumference, three uniformly spaced apart radial projections 19, which together define a circle diameter that is increased in comparison with that of the upstanding portion 18. This increased diameter is substantially reflected by the inside diameter of the carrier 17; thus accordingly the carrier 17 is guided along the radially outer surfaces of the projections 19.

At the side away from the intermediate base 10, the carrier 17 is provided along its radially inner peripheral edge with a radially inwardly protruding annular collar 20, by way of which the carrier 17 at the same time engages on the central upstanding portion 18 along its circumferential peripheral edge. This radial collar 20 is significantly reduced in terms of material in the thickness direction, i.e. seen in the direction of the x axis, it accordingly having a thickness which corresponds approximately to one fifteenth to one twentieth of the corresponding thickness of the carrier.

At the surface which in the assembled state faces the end wall 9 covering over the carrier 17, the carrier 17 is provided with receiving bores 21. In the exemplary embodiment represented, there are altogether 15 receiving bores 21 uniformly spaced apart from one another in the circumferential direction, having the same diameter and disposed on a common diameter line. Each of these receiving bores 21 opens out in a transverse channel 22. The transverse channels 22, of which there are likewise altogether fifteen, are separated from one another and respectively aligned strictly radially in relation to the x axis, each transverse channel 22 also opening out fully, both radially inwardly and radially outwardly.

Each radially outer mouth region of the transverse channels 22 is concavely curved as seen in plan view, so that the mouth opening of the transverse channel 22 is set back radially with respect to the outer diameter line of the carrier 17. The diameter of the concave regions 23 is selected such that a portion of the original carrier diameter remains between each two adjacent transverse channels 22.

Radially inwardly facing notches 24 are formed in each of these regions which remain between two transverse channels 22 and have the original carrier diameter. These notches take the form of radial slits. The outside diameter of the carrier 17 substantially corresponds to the inside diameter of the lateral wall 5 of the housing middle part 11.

The carrier 17 serves for receiving and transporting a blister pack 25. The latter is formed in a way similar to the carrier 17 as a circular ring, with an outside diameter adapted to the inside diameter of the lateral wall 5. The inside diameter of the blister pack 25 substantially corresponds to that of the carrier 17.

In the usual way, the blister pack 25 comprises a plastics annular part 27, defining cavities 26, and a laminated-on layer 28 of an aluminum foil. The cavities 26 are each formed by substantially hemispherical domes 29 formed from the plastics material. A pre-apportioned quantity of the substance 30 to be inhaled is accommodated in each cavity 26. The laminated-on aluminum foil layer 28 forms the base of the cavity. The blister pack 25 is provided with cavities 26 corresponding to the number of receiving bores 21, thus in the exemplary embodiment represented, with fifteen such cavities 26, which are disposed uniformly spaced apart from one another in the circumferential direction on a common diameter line. The respective dome diameter corresponds substantially to the diameter of a receiving bore 21.

When the cavities 26 face the carrier 17, the blister pack 25 is positively fixed, and consequently rotationally fixed with respect to the carrier 17, by the domes 29 being inserted into the receiving bores 21 of the carrier 17. Passing through the receiving bore 21, each cavity 26 or each dome 29 thereby protrudes into the respective transverse channel 22 of the carrier 17, substantially closing this transverse channel 22 when the filled dome 29 is intact.

Associated with each cavity 26, the blister pack 25 is provided on the free surface of the aluminum foil layer 28 with an identification (not represented), thus for example, in the case of fifteen cavities 26, beginning with the numeral 15 and counting down over the further cavities 26, which identification can be visually ascertained through the viewing window 13. This provides the user with, in particular, information on the number of inhalation portions that are still present.

The blister 25 is held on the central upstanding portion 18 of the intermediate base 10 by means of a disk-shaped fixing part 12, with the thinned radially inner annular collar 20 of the carrier 17 being clamped, for which purpose positive connecting means 16 passing through the part 12 engage in the upstanding portion 18. The latter may also be molded-on in one piece on the fixing part 12.

After lifting off the latched end wall 9 and removing the fixing part 12, the blister 25 is exposed to allow it to be exchanged.

Figure 10:
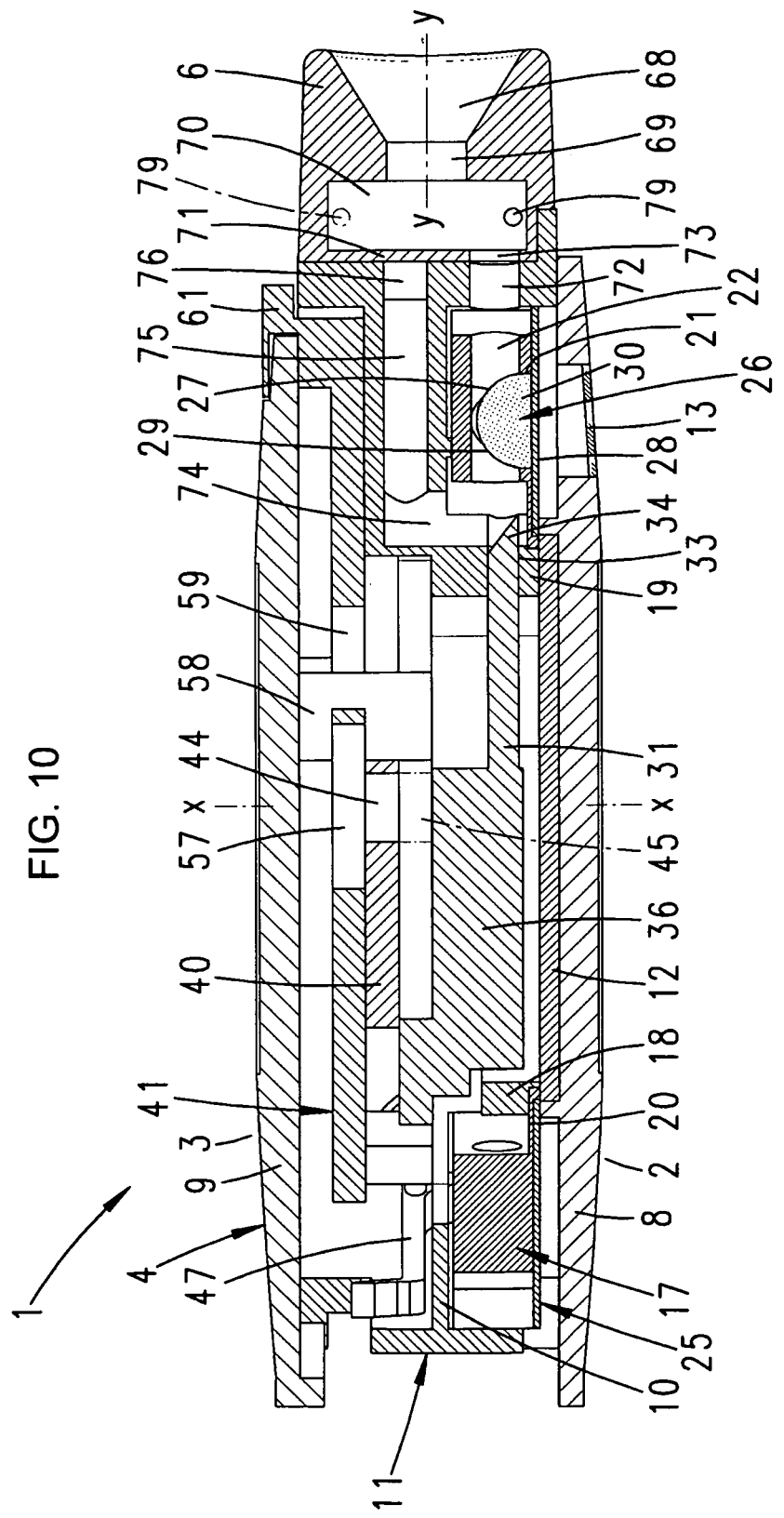
FIG. 10 shows the longitudinal section along the line X-X in FIG. 9.

For the delivery of the substance 30 stored in each cavity 26, it is first necessary for the cavity 26 to be opened. This opening is effected in the case of the proposed dispenser 1 by punching holes, thus according to the invention by punching holes in the dome 29 when this is in the ready position. For this purpose, a needle 31 that can be brought into the hole-punching position is provided. This needle lies in a radially aligned, slit-like recess 32 in the intermediate base 10, which slit-like recess 32, seen in its direction of extent, extends over a great part of the diametral dimension of the central upstanding portion 18, crossing over the x axis while leaving a closed peripheral portion. The needle 31 lies in the plane defined by the transverse channels 22 of the carrier 17. In an extension of the recess 32 on one side, said recess changes into a radial bore 33, which runs in the same direction and is adapted in diameter to the outside diameter of the needle 31. The needle 31 lies in a guided manner in this radial bore 33, the radial bore 33 also passing, seen in the circumferential direction, centrally through one of the radially widened portions 19 of the upstanding portion 18, to be aligned in prolongation with a transverse channel 22 of the carrier 17 (cf. for example FIG. 10). When seen in plan view, the tip 34 of the needle 31 points radially outwardly in the direction of the mouthpiece 6, passing through the radial bore 33; also when seen in plan view, it is aligned with a mouthpiece channel axis y, which is aligned perpendicularly to the dispenser x axis.

The needle 31 has a diameter which, in the exemplary embodiment represented, corresponds to approximately half the radius of a dome 29. Furthermore, the planar way in which the needle 31 is disposed is selected so that the tip 34 of the needle, which is pointed in the manner of a cannula, though solidly formed, passes through the dome 29 in the direction of the diameter of the dome and is aligned parallel with the aluminum foil layer 28, in order to form two oppositely-located holes that are accordingly aligned coaxially with the axis of the needle and in addition also coaxially with the axis of the transverse channel. The aluminium foil layer 28 remains unaffected by this.

Figure 20:
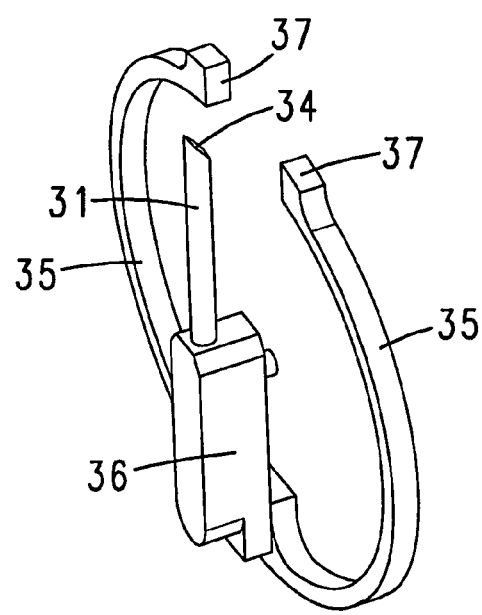
FIG. 20 shows the needle with molded-on springs, in perspective individual representation.

The needle 31 is provided at its foot, i.e. in the end region remote from the tip 34, with spring arms 35 that are molded-on, in particular formed in one piece with the needle 31, by the plastics injection-molding process. As can be seen in FIG. 20, these spring arms 35 are rooted in the region of a basic body 36 that also carries the needle 31. Seen in plan view, the spring arms 35 extend from this basic body 36 in the same way on each side and are respectively curved outward in the form of a semicircular ring to form free spring ends 37, which, in the unloaded state according to the individual representation in FIG. 20, are placed adjacent the tip 34 of the needle on both sides when seen in plan view. By means of these spring ends 37, support is provided on supporting shoulders 38, which are associated with the mouthpiece 6 region, are provided on the inner side of the lateral wall 5, and are also overlaid by cover portions 39 formed in one piece from said shoulders, to secure the spring ends 37.

As a result of this configuration, when the needle is advanced in the direction of the mouthpiece 6, for piercing the associated cavity 26 with the tip 34 of the needle, the spring arms 35 are stressed, as a result of which spring loading an automatic return displacement of the needle 31 into the starting position can be achieved. This rearward basic position is stop-limited, by the basic spring body 36 abutting against the remote end of the recess 32 remote from the mouthpiece 6.

The deliberate advance of the needle 31 for piercing the associated dome 29 takes place by means of a lever arrangement. This substantially comprises a lever-like drag part 40 and a disk-like actuating element 41.

The drag part 40, lying flat on the basic needle body 36, is associated with a peripheral region of the middle part 11 and is articulated on it, for which purpose a pivot pin 42 extends from the middle part 11. The drag part 40 can be displaced in a pivoting manner about this pivot pin. At the other end, the drag part 40 has an integrally-formed drag nose 43, for interaction with the actuating element 41. In the region where it crosses the needle 31, aligned transversely to the drag part 40, the drag part 40 is provided with a slot-like recess 44, in which there engages a driving pin 45, which is formed on the basic body 36 and is aligned parallel to the pivot pin 42.

The disk-shaped actuating element 41 has, associated with a peripheral portion 2, actuating portions, which interact reciprocally with one another and each of which acts in the circumferential direction. This means that, when one actuating portion is being used, the other actuating portion is inactive, and vice versa. Each of these actuating portions 46, 47 is cut free by a radial incision and a subsequent arcuate incision. Accordingly, the actuating portions 46 and 47 of the actuating element 41, which are preferably formed by the plastics injection-molding process, are configured in such a way that they can yield perpendicularly to the extent of the surface area of the actuating element 41, this also taking place with material-dependent spring loading of the portions into the basic position, i.e. in the direction of the common plane of the portions and the actuating element 41.

The two actuating portions 46 and 47 extend from a common root region 48; they extend from this in opposite circumferential directions. Also molded onto this root portion 48 is a handle 49. This engages through a correspondingly positioned slot-like cut-out 50 in the lateral wall 5 of the housing middle part 11, as a result of which the handle 49 protrudes outwardly and is consequently freely accessible. The handle 49 lies here in a reduced-diameter middle region of the lateral wall 5, so that the handle 49 does not protrude, or does not protrude significantly, beyond the overall contour of the dispenser 1 or of the dispenser housing 4, but can nevertheless be easily grasped.

In a basic position, the actuating portion 46, this extending freely counterclockwise as seen in a plan view of the actuating element 41, which is disposed in a plane above the drag part 40, is in positive engagement with the drag part 40. For this purpose, the actuating portion 46 has, on its underside, facing the drag part 40, a driving nose 51. In the driving position, the counterclockwise-directed end face extends substantially perpendicularly to the plane of extent of the actuating element 41 and butts against the similarly directed facing surface of the drag nose 43 on the drag part.

The actuating portion 47, which extends freely clockwise from the root portion 48, forms at the end a drive finger 53, pointing downwardly in the direction of the blister carrier 17. This drive finger passes through the plane of the housing middle part 11 in the region of a cut-out 52, which is near the periphery and is taken out from the intermediate base 10.

The drive finger 53 is provided on its end face, i.e. at the front when seen in the clockwise direction, with a surface running perpendicularly to the plane of the actuating element, while the surface to the rear of this, acting in the clockwise direction, forms a run-on slope.

Pointing radially inward, a disengaging pin 54 is molded onto the drive finger 53, or on the actuating portion 47 carrying the latter. This disengaging pin protrudes freely into the cut-out that is left to form the actuating portion 47.

Together with a restraining finger 55, fixedly secured in place on the housing middle part 11 in the radially outer region of the intermediate base 10, near the inner wall of the lateral wall 5, the drive finger 53 of the actuating element 41 forms a stepping mechanism 56 for the step-by-step displacement of the carrier 17 and the blister 25 accommodated in it.

The disk-like actuating element 41, which can be actuated by means of the handle 49, is suitable for the rotational displacement.

Aligned coaxially with a central bore 57, a slot-like cut-out 59 in the form of a segment of a circle is formed from the surface-area part of the actuating element 41 and in this cut-out there engages a pin 58, molded onto the front end wall 8 on the inner side of the housing to provide the stop limitation on both sides for the pivoting capability of the actuating element 41. This pin extends in terms of its length as far as the intermediate base and, facing the latter, forms a fixing sleeve that is aligned with a through-opening in the intermediate base. Engaging positively in this sleeve is a pin 60, passing through the intermediate base 10, for the operationally non-detachable fixing of the end wall 8.

Lying diametrically opposite the handle 49, the actuating element 41 carries a pointer-like blocking lug 61. This engages through a slit left at the periphery between the lateral wall 5 and the front end wall 8 and, with a radially inwardly facing overlying portion, overlies a portion of the end wall 8 in this region that is circumferentially matched in length to the possible path of pivoting of the actuating element 41 and is reduced in terms of thickness.

The pointer-like blocking lug 61 provides the user with a visual indication of the current operating position of the dispenser 1. Furthermore, the blocking lug 61 interacts with the closure cap 7 of the mouthpiece 6 as a safeguard against closing of the mouthpiece 6 in a position which is not the ready position.

Figure 15:
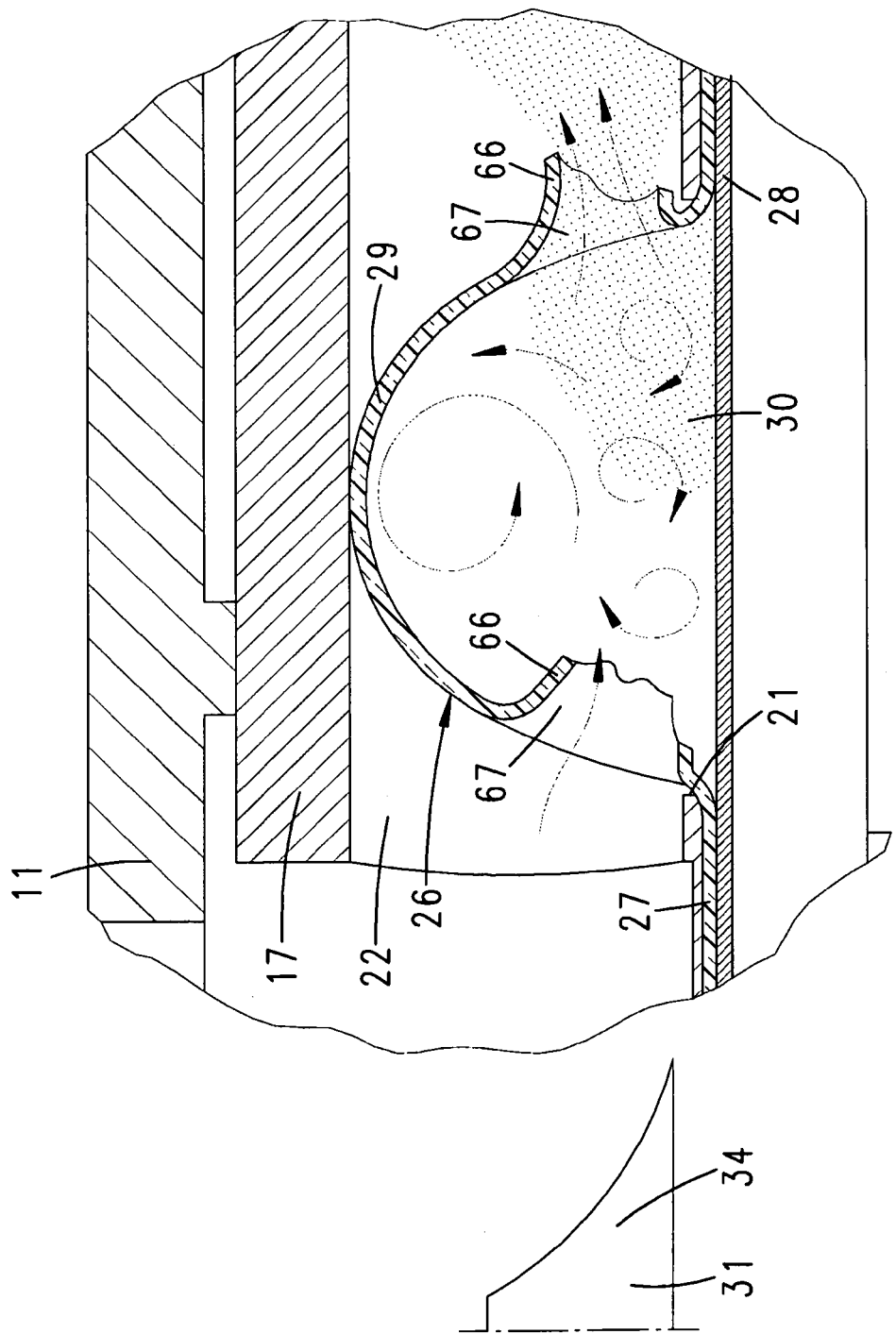
FIG. 15 shows the enlargement taken from the region XV in FIG. 14.
Figure 16:
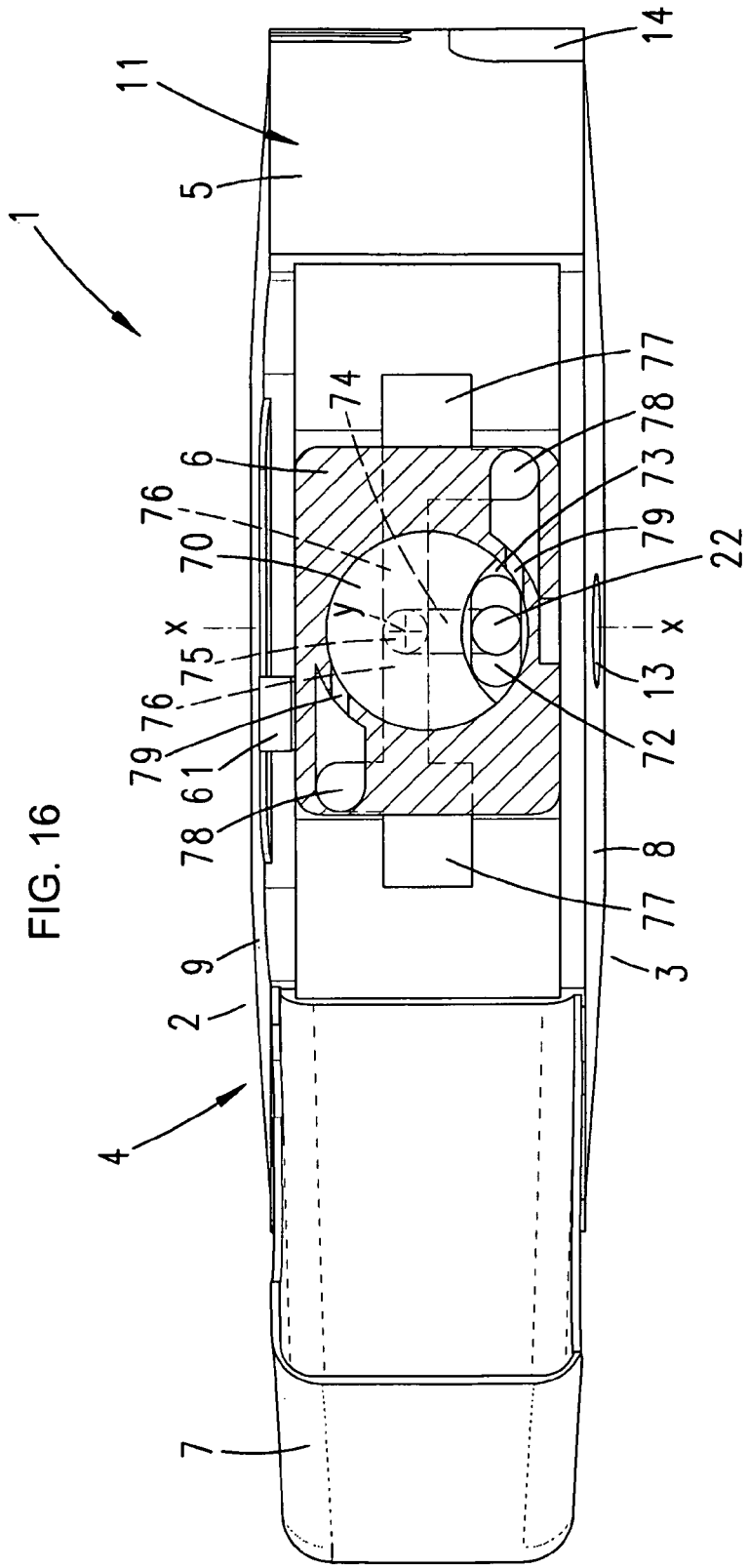
FIG. 16 shows the section along the line XVI-XVI in FIG. 14.

From a ready position, in which an intact, filled cavity is associated with the radial bore 33 of the intermediate base 10 that is passed through by the tip 34 of the needle, preparation for inhalation is effected by punching holes in the respective dome 29. For this purpose, the user grasps the handle 49 and displaces it counterclockwise with respect to a plan view of the front end wall 8 of the dispenser 1. Accompanying this, the actuating element 41 is rotationally displaced about the x axis, taking the drag part 40 with it on account of the drag connection between the driving nose 51 of the actuating portion 46 and the drag nose 43 of the drag part 40 that exists during the course of the rotational displacement. As a result of the rotational mounting of the drag part 40 lying opposite the drag connection, the driving pin 45, carried along by way of the slot-like recess 44, moves transversely in relation to the direction of the x axis, this leading to the molded-on needle 31 being advanced. The latter thereby penetrates into the associated transverse channel 22 of the carrier 17. With further advance, the tip 34 of the needle initially pierces a first wall portion of the dome and, after passing through the dome 29, pierces the diametrically opposite wall portion. The piercing of the dome wall thereby takes place near the diameter line of the dome, i.e. near where it is joined to the aluminum foil layer 28 or near where it is supported around the edge on the periphery of the bore in the carrier 17 (cf. in this respect FIG. 15).

The actuating portion 46 drives the drag nose 43 of the drag part 40 along until piercing of the dome 29 has been completed, and the free end face 62 of the actuating portion, which forms a run-on slope, then reaches a disengaging pin 63 protruding radially inward on the inside of the lateral wall 5. In interaction with the control surface 62, this pin leads during the course of further counterclockwise rotational displacement of the actuating element 41 to a vertical release of the actuating portion 46, and when this vertical displacement has been completed, the driving nose 51 releases the drag nose 43 on the drag part.

Figure 11:
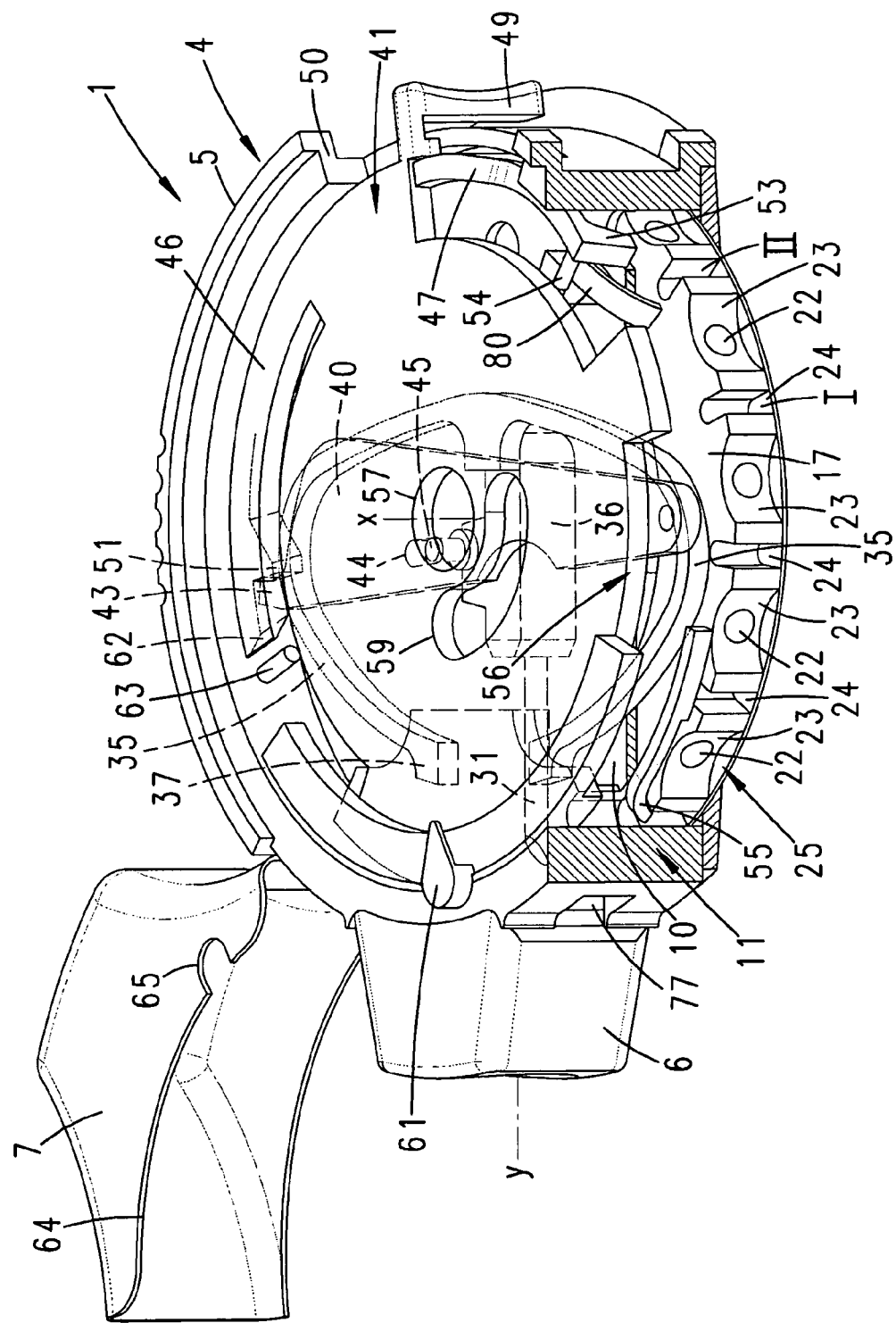
FIG. 11 shows a representation corresponding to FIG. 9, but during the course of a manually actuated needle displacement to expose a cavity.
Figure 12:
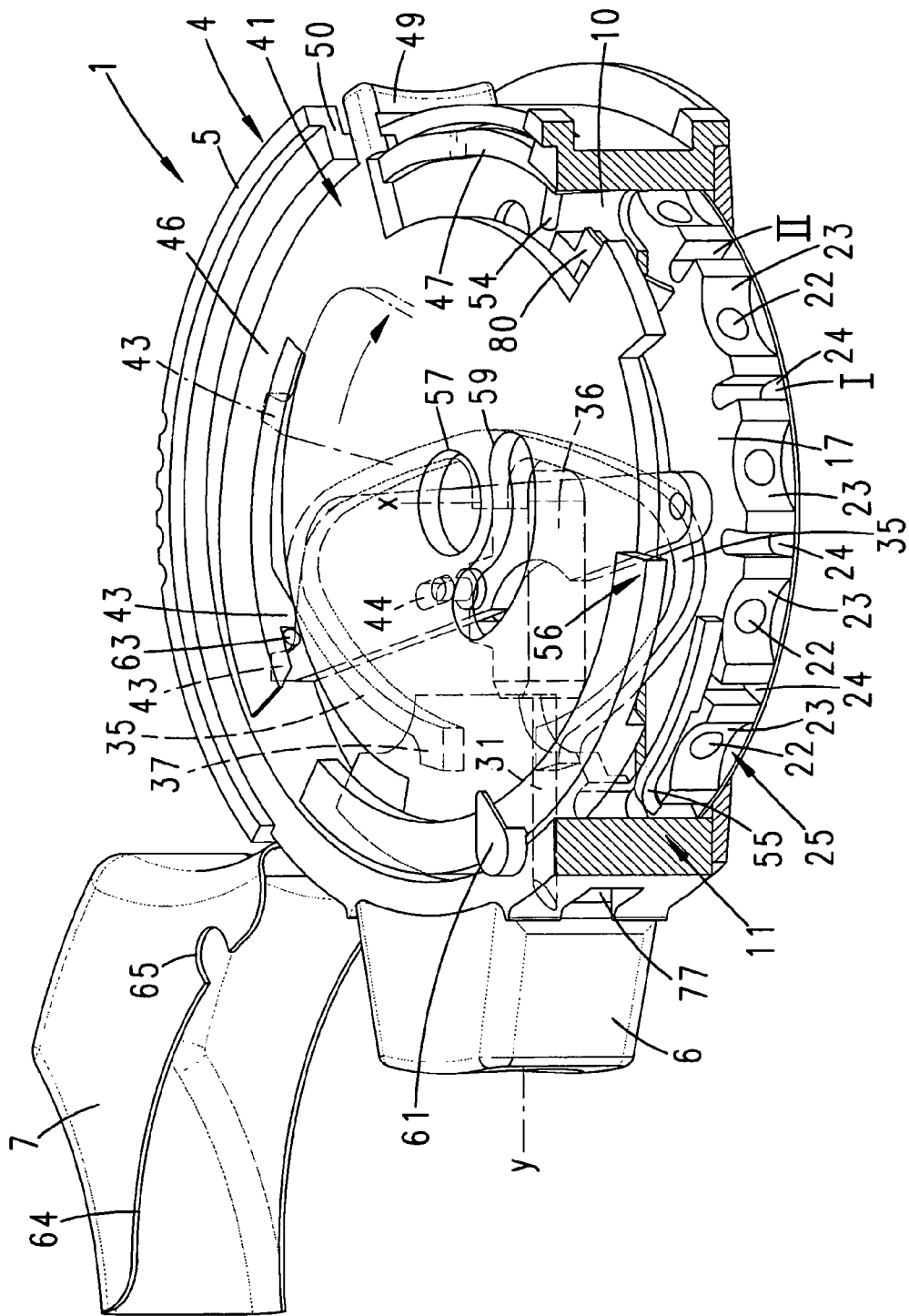
FIG. 12 shows a representation following on from FIG. 11.
Figure 13:
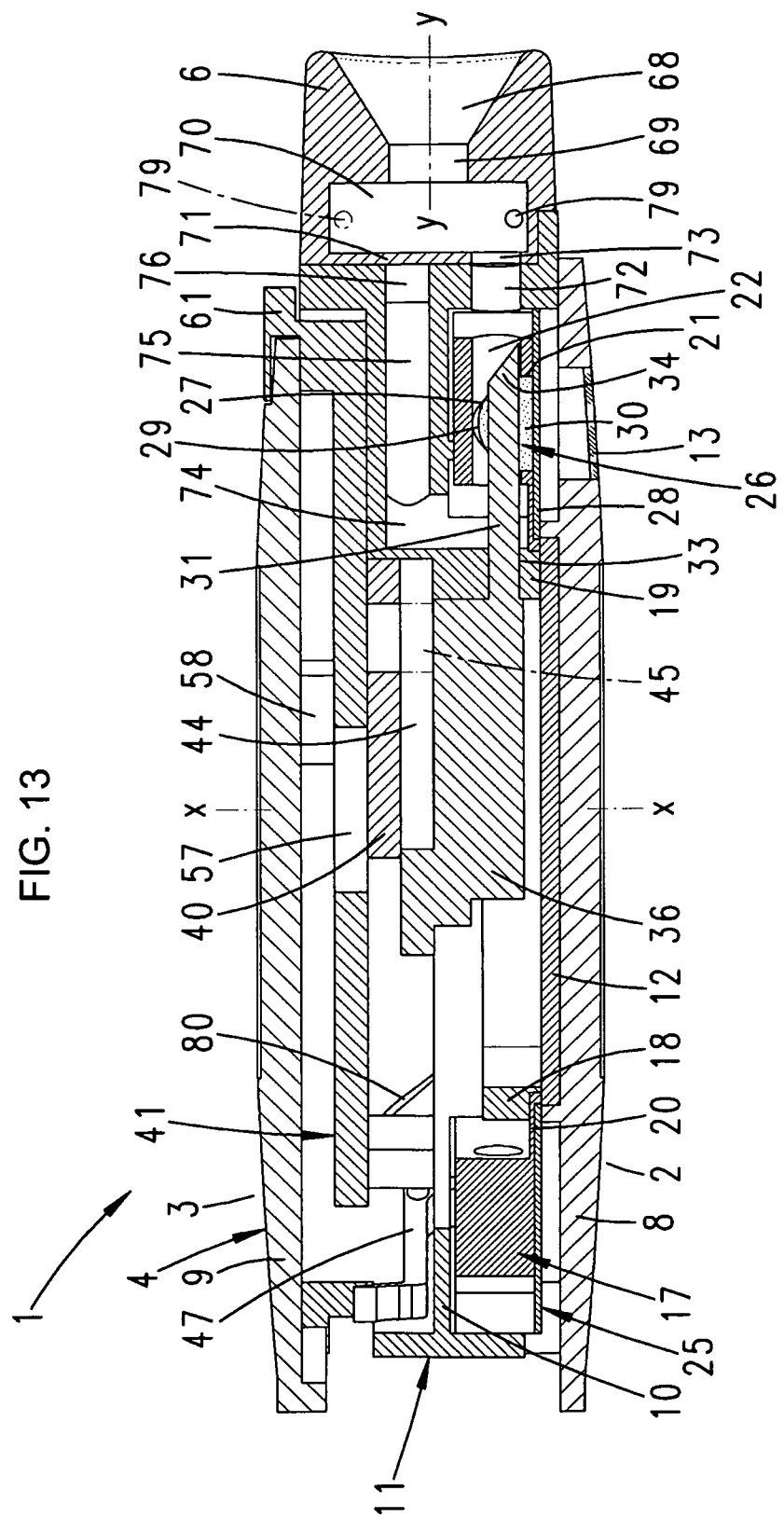
FIG. 13 shows a sectional representation according to FIG. 10, but in the position when the dome-shaped cavity is being pierced.
Figure 14:
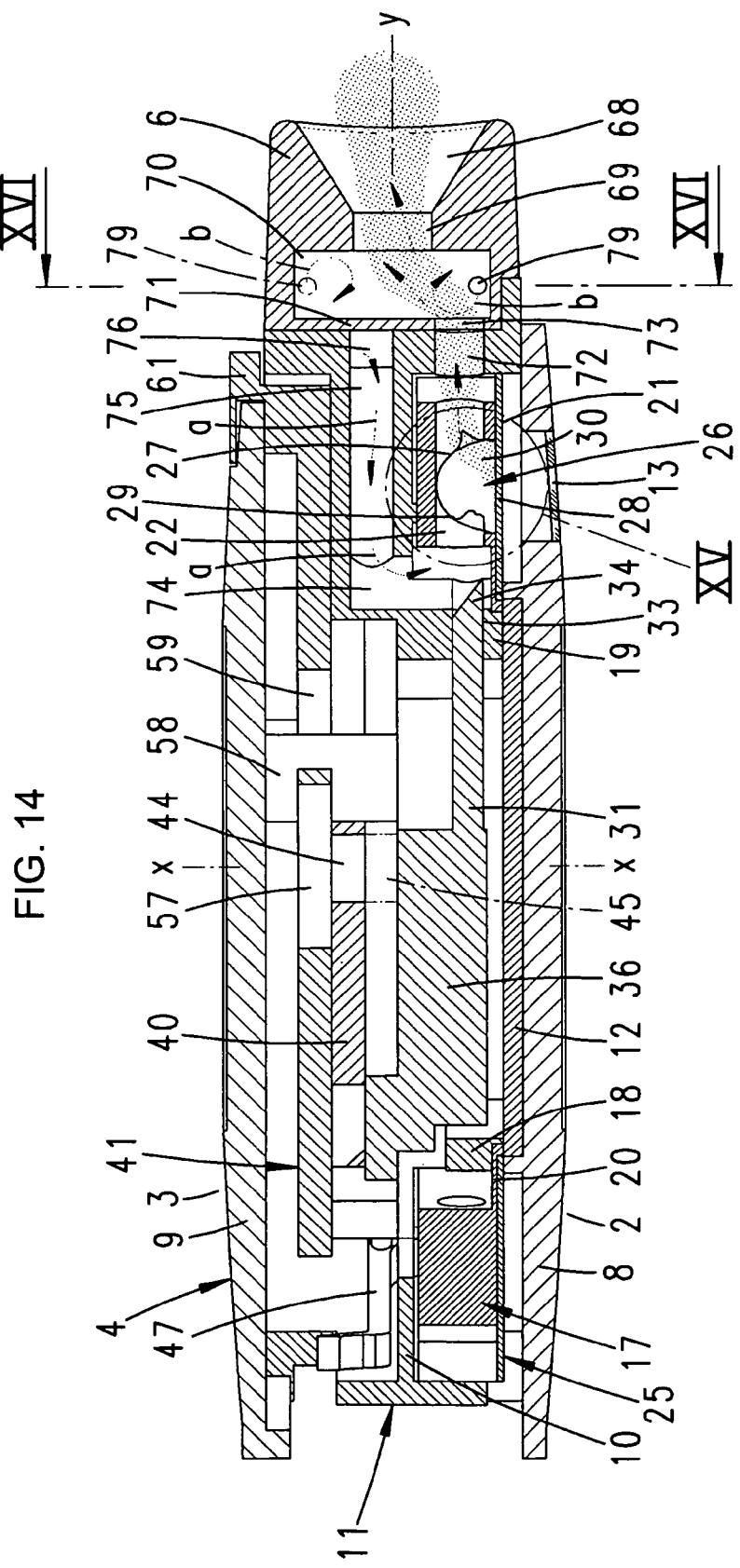
FIG. 14 shows a representation following on from FIG. 13 after piercing and return displacement of the needle into the basic position have taken place, and when an inhalation operation has been indicated.

After deactivation of the drag connection between the actuating portion 46 and the drag part 40, the spring arms 35 (cf. FIGS. 11 and 12), tensioned during the course of the needle advance, lead to a triggered, automatic return displacement of the needle 31 into its starting position, while the spring arms 35 are relieved of stress.

The piercing of the dome 29 takes place even before the stop-limited rotational end position of the actuating element 41 is reached. Accordingly, when it reaches its end position, or shortly before that, the needle 31 quickly returns in a spring-assisted manner. This stop-limited end position is also evident to the user. The pointer-like blocking lug 61 assumes a position that is changed with respect to the basic position, corresponding to the path of pivoting of the handle 49 and the actuating element 41. In this position, closing of the closure cap 7 is not possible, since the edge of the cap butts in this position against the blocking lug 61, the edge of the cap in this case forming a blocking shoulder 64. Closing of the closure cap 7 is only possible in the opposite end position. In this position, the blocking lug 61 interacts with an open-edged recess 65 in the rim of the cap.

Any particles of substance that may be forced out of the cavity 26 when the dome 29 has been pierced by the needle 31 are not lost to the following inhalation operation during this action, since they are introduced into the transverse channel 22, which, during the course of the inhalation, becomes part of the suction air stream channel. During the course of the automatic, spring-assisted return displacement of the needle 43, wiping off of the surface of the needle is achieved by the chads 66 occurring in the direction of piercing in the region of the dome holes 67.

The apportioned substance 30 stored in the cavity 26 then lies freely in the suction air stream channel, ready for inhalation. This inhalation is effected orally in the case of the dispenser represented. For this purpose, the mouthpiece 6 has centrally, coaxially with the y axis, a radially outwardly widening outlet funnel 68. This initially changes into a central intermediate portion 69 of reduced diameter, which opens out in a once again radially widened swirl chamber 70. This swirl chamber 70 has a chamber base 71. This chamber base is provided with a window-like opening 73, associated with a suction channel portion 72 formed in extension of the radial bore 33 of the intermediate base 10 in the lateral wall 5 of the housing 4.

The opening 73, the suction channel portion 72 and the transverse channel 22 of the carrier 17 that is brought into the operative position are disposed one after the other and accordingly form a straight suction channel running parallel to the y axis. At the foot, i.e. remote from the mouthpiece 6, further associated with the radial bore 33 passed through in a sealing manner by the needle 31, the suction channel changes into a deflecting channel 74, which runs in parallel alignment with the x axis, is formed in the intermediate base 10 and changes again into a channel portion 75 directed back in the direction of the mouthpiece 6. This is likewise aligned in a straight line and extends in a central plane with respect to the x axis; it is formed from the fully solid intermediate base 10.

The channel portion 75 and the further channel portion that is made up of the suction channel portion 72 and substantially the transverse channel 22 are disposed such that they lie one over the other and are connected to each other by way of a 180° deflection.

The channel portion 75, covered by the chamber base 71, opens out into intake channel portions 76 extending on both sides, in each case approximately in the circumferential direction of the lateral wall 5. These portions accordingly extend underneath the mouthpiece 6 transversely in relation to the channel portion 75 and, as can be seen for example from the representation in FIG. 4, end laterally of the mouthpiece 6, open toward the outside after passing through the lateral wall 5. Air is sucked in via these intake openings 77 by breathing in during the course of inhalation.

Figure 19:
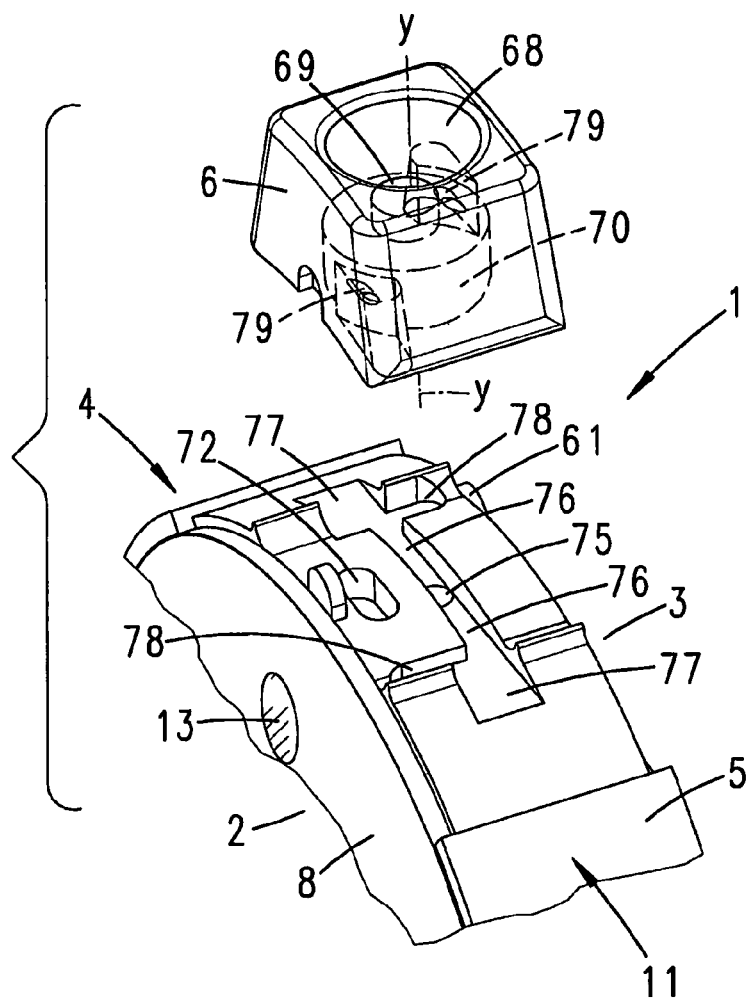
FIG. 19 shows the mouthpiece and the housing region associated with the mouthpiece in perspective representation, to show the flow paths.

As can also be seen in particular from the representation in FIG. 19, branch channels 78 respectively extend from the intake channel portions 76. These branch channels are in flow communication with nozzle-like bypass openings 79, passing tangentially through the lateral wall of the swirl chamber 70.

The inhalation is effected, after piercing of the dome 29, by sucking in via the mouthpiece 6. Air is thereby sucked radially inward of the dispenser 1 via the intake openings 77 and the transversely directed intake channel portions 76, initially via the channel portion 75, and after that through the associated transverse channel 22 of the carrier 77 while undergoing 180° deflection. The air flowing through the transverse channel 22 is made to pass through the opened dome 29, from which it carries the particles of substance out, while they undergo advantageous swirling within the dome 29, and transports them via the suction channel portion 22, the swirl chamber 70 and the intermediate portion 69 to the outlet funnel 68 (arrows a), swirling at the walls, in particular of large particles of substance, also being achieved in the swirl chamber 70 region by means of the bypass openings 79. The additional horizontal swirls (arrows b) ensure good distribution.

The way in which the dome 29 is opened according to the invention by piercing diametrically opposite wall portions of the dome without damaging the aluminum foil layer 28 forming the base achieves complete emptying, and consequently also ensures inhalation of a correctly apportioned amount.

As mentioned, closing of the mouthpiece closure cap 7 cannot be achieved from this position. As a result, the user is provided with a safeguard that indicates to him that, although the dome has been pierced, the inhalation operation has not yet been carried out or the dispenser 1 has not yet been prepared for the next inhalation operation.

This preparation is effected by rotational return displacement of the actuating element 41 by means of the handle 49 counter to the rotational direction necessary for punching the holes, that is to say now in a clockwise direction with reference to the viewpoint described. This is where the stepping mechanism 56 comes into use. Its fingers 55 and 53 interact with the peripheral notches 24 of the carrier 17, the restraining finger 55 only allowing, by its design, clockwise rotation of the carrier 17 in the exemplary embodiment represented.

The step-by-step displacement of the carrier 17 is achieved by means of the driving finger 53. This finger is deflected vertically upward by means of its disengaging pin 54 during the course of the needle advance, i.e. when the actuating element 41 rotates counterclockwise. For this purpose, a run-up slope 80 is formed on the intermediate base 10. By means of this slope, the driving finger 53 is brought into a plane above the carrier 17, the disengaging pin 54 leaving the run-up slope 80 in the further course of the counterclockwise rotational displacement, which brings about the vertical dropping of the driving finger 53 onto a portion of the intermediate base that overlies the carrier 17.

Figure 17:
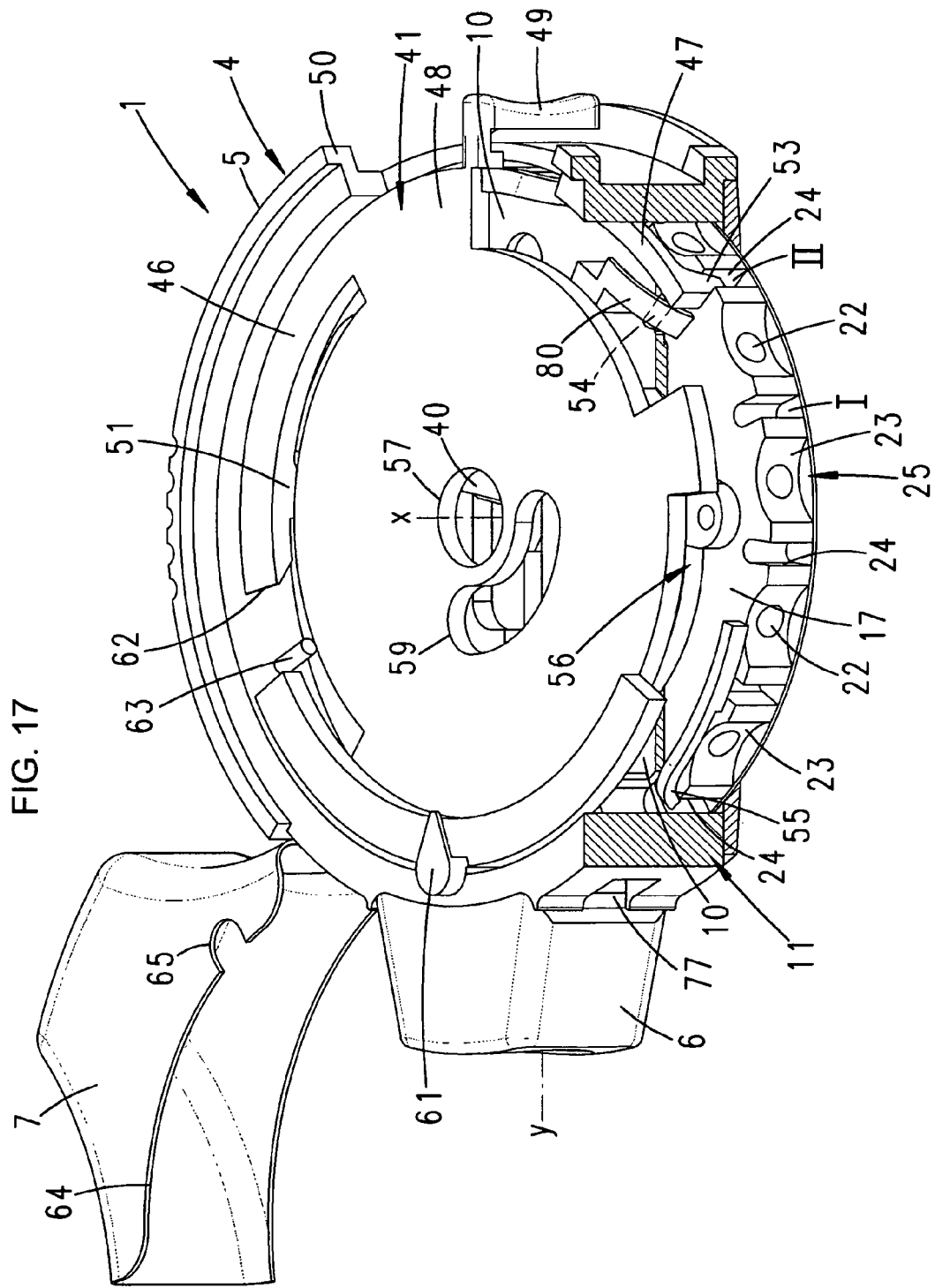
FIG. 17 shows a further perspective representation according to FIG. 9, but for a representation following on from FIG. 12, when manual actuation of the stepping mechanism is effected, after an inhalation.
Figure 18:
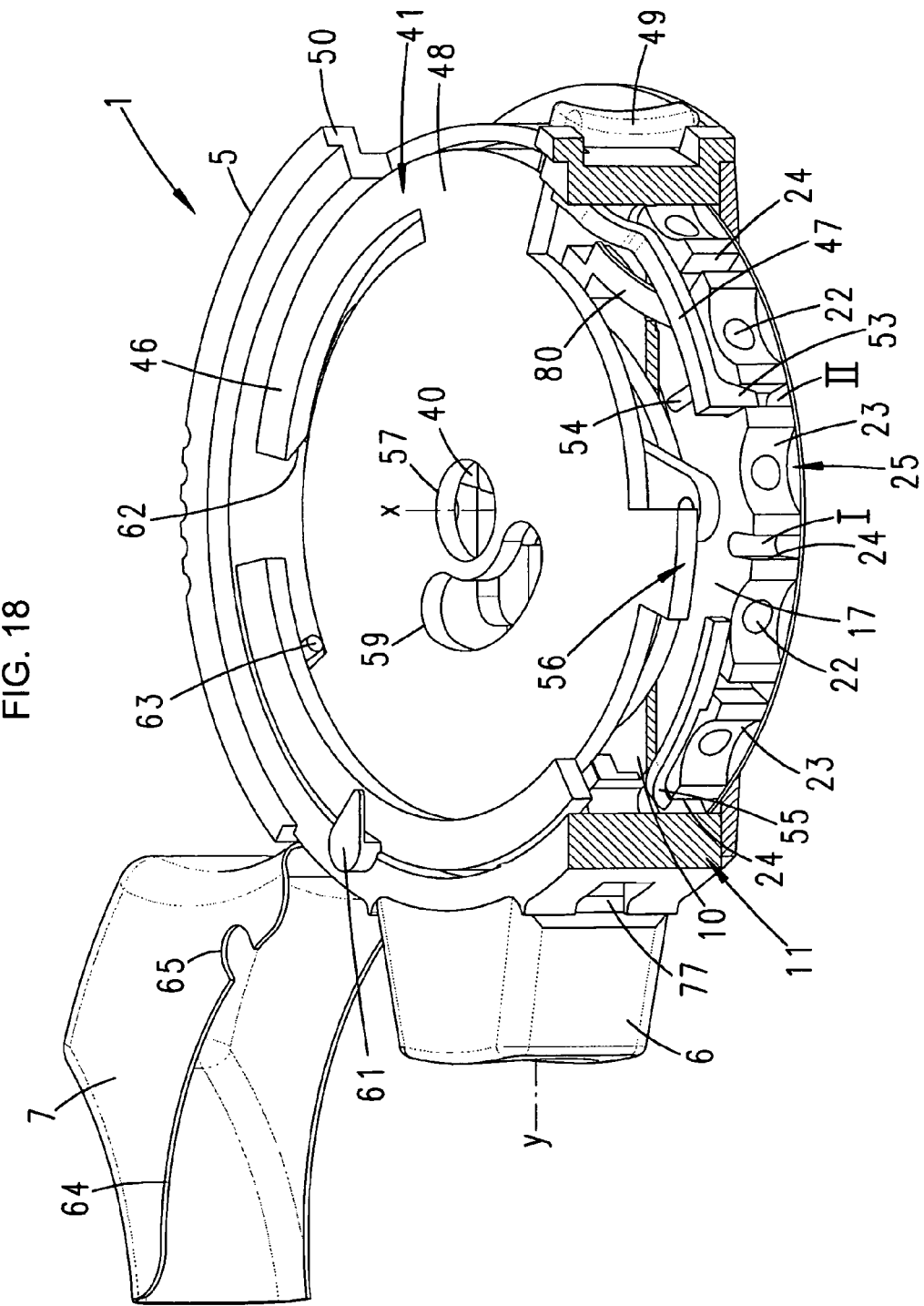
FIG. 18 shows a representation following on from FIG. 17, when the basic position has been reached.

Only the rotational return displacement of the actuating element 41 in the clockwise direction leads to relinquishment of the support of the driving finger 53 on the portion of the intermediate base. As a result of the appropriate configuration of the actuating portion 47, the driving finger 53 drops vertically in the direction of the carrier 17 with spring assistance, to fall into the next notch 24 in the clockwise direction. This finger engagement is also assisted by the molded-on disengaging pin 54 being acted upon from above by the underside of the portion forming the run-on slope 80 on the upper side (cf. FIG. 17). This portion forming the run-on slope 80 is formed such that it can resiliently yield, so that during the further course of the rotation, the driving finger 53, now dragging along the carrier 17, can reach with its disengaging pin 54 under this portion, after which the disengaging pin 54 is once again aligned facing the run-on slopes 80 for the next displacement in the counterclockwise direction.

After this stepped displacement of the carrier 17 (represented by way of example by the step positions I and II), the next cavity is associated with the suction channel portion 72 and the needle 31.

This is also the position in which closing of the mouthpiece 7 can be achieved.

After running over the drag nose 43 on the drag part, the driving nose 51 is again in a driving position in relation to the drag nose 43; ready for the next hole-punching operation.

All features disclosed are (in themselves) pertinent to the invention. The disclosure content of the associated/accompanying priority documents (copy of the prior application) is hereby also incorporated in full in the disclosure of the application, including for the purpose of incorporating features of these documents in claims of the present application.

The invention claimed is:

1. A dispenser for dispensing pulverulent substances, comprising:
    a dispenser housing having a mouthpiece;
    a circular blister pack having a center and being movably disposed in said dispenser housing, said blister pack having a plurality of domes disposed radially about said center and forming dome-shaped cavities on a base layer, said domes having mutually opposite lateral walls and being disposed for moving said dome-shaped cavities, by movement within said dispenser housing, into an emptying position;
    a needle movably disposed in said dispenser housing for opening said dome-shaped cavities in said emptying position for emptying by a suction air stream leading to said mouthpiece, said needle having elastically yielding spring arms formed thereon at an end thereof remote from a tip of said needle;
    said needle being disposed to pass crosswise through said dome in a direction from said center radially outwards for piercing punched holes into and passing through said opposite lateral walls of said dome and wherein, after retraction of said needle, said punched holes lie in a path of the suction air stream channel leading to the mouthpiece.

2. The dispenser according to claim 1, wherein all of said domes penetrate into respective individual accommodating holes in a carrier and close off a transverse channel of said carrier, prior to piercing by said needle.

3. The dispenser according to claim 1, wherein said base layer is an annular base layer.

4. The dispenser according to claim 1, wherein said needle pierces said later walls of said dome along a straight line extending substantially along a diameter line.

5. The dispenser according to claim 1, wherein a diameter of said needle corresponds to one sixth to one third of a diameter of said dome.

6. The dispenser according to claim 1, wherein said needle is disposed to run through said dome wall near a base layer of said cavities.

7. The dispenser according to claim 1, wherein said needle passes through said dome while building up a spring force and wherein, after passing through said dome, said needle returns automatically, triggered by a release of the spring force.

8. The dispenser according to claim 1, wherein a triggering of the needle return displacement takes place automatically.

9. The dispenser according to claim 1, which comprises a drag part for moving said needle into a piercing position.

10. The dispenser according to claim 9, which comprises an actuating element coupled to a user-accessible handle, for displacing said drag part in a triggerable manner.

11. The dispenser according to claim 1, wherein said needle is formed in one piece with said spring arms.

12. The dispenser according to claim 1, wherein said needle is a solid plastic, injection-molded component formed with said spring arms.

13. The dispenser according to claim 1, which comprises a stepping mechanism, for moving said dome-shaped cavities step by step into said emptying position, and a user-actuated actuating element for piercing said dome-shaped cavities with said needle, said stepping mechanism interacting with said actuating element.

14. The dispenser according to claim 13, wherein said stepping mechanism is an integral part of said actuating element.

15. The dispenser according to claim 1, wherein, once a cavity has been emptied, said carrier accommodating the blister is advanced by one step during a course of a return displacement of said actuating element that is to be carried out manually.

16. The dispenser according to claim 1, which further comprises a mouthpiece closure cap, which is connected in a controlling manner to the annular blister carrier driven by a stepping mechanism.

17. The dispenser according to claim 16, which further comprises a blocking lug disposed in a rotationally fixed manner on said actuating element and disposed for interaction with said mouthpiece closure cap.

18. The dispenser according to claim 17, wherein said mouthpiece closure cap is formed with a recess which is open at an edge, for said blocking lug to enter in a ready position of the dispenser.

19. The dispenser according to claim 18, wherein said mouthpiece closure cap has a blocking shoulder at a spacing from said recess which interacts with the blocking lug in an unready position.

20. The dispenser according to claim 1, wherein said housing has a swirl chamber formed therein and, before the suction air stream leaves said mouthpiece, the suction air stream transporting the substance passes through said swirl chamber.

21. The dispenser according to claim 1 configured as a medicament dispenser.

22. A dispenser for dispensing pulverulent substances, comprising:

a dispenser housing having a mouthpiece;

an annular blister pack movably disposed in said dispenser housing, said blister pack having a plurality of domes forming dome-shaped cavities disposed in a circular arrangement on a base layer, said domes having lateral walls and being disposed for indexing said dome-shaped cavities, by movement within said dispenser housing, into an emptying position;

a needle movably disposed in said dispenser housing for opening said dome-shaped cavities in said emptying position for emptying by a suction air stream leading to said mouthpiece said needle having elastically yielding spring arms formed thereon at an end thereof remote from a tip of said needle;

wherein said needle is disposed to pass from a center of said annular blister pack radially outwardly, to pass through said lateral wall and pierce a punched hole into said dome, and wherein, after retraction of said needle, said punched hole lies in a path of the suction air stream channel leading to said mouthpiece.

23. The dispenser according to claim 22, wherein all of said domes penetrate into respective individual accommodating holes in a carrier and close off a transverse channel of said carrier, prior to piercing by said needle.

24. The dispenser according to claim 22, wherein said base layer is an annular base layer.

25. The dispenser according to claim 22, wherein said needle pierces said later walls of said dome along a straight line extending substantially along a diameter line.

26. The dispenser according to claim 22, wherein a diameter of said needle corresponds to one sixth to one third of a diameter of said dome.

27. The dispenser according to claim 22, wherein said needle is disposed to run through said dome wall near a base layer of said cavities.

28. The dispenser according to claim 22, wherein said needle passes through said dome while building up a spring force and wherein, after passing through said dome, said needle returns automatically, triggered by a release of the spring force.

29. The dispenser according to claim 22, wherein a triggering of the needle return displacement takes place automatically.

30. The dispenser according to claim 22, which comprises a drag part for moving said needle into a piercing position.

31. The dispenser according to claim 30, which comprises an actuating element coupled to a user-accessible handle, for displacing said drag part in a triggerable manner.

32. The dispenser according to claim 22, wherein said needle is formed in one piece with said spring arms.

33. The dispenser according to claim 22, wherein said needle is a solid plastic, injection-molded component formed with said spring arms.

34. The dispenser according to claim 22, which comprises a stepping mechanism, for moving said dome-shaped cavities step by step into said emptying position, and a user-actuated actuating element for piercing said dome-shaped cavities with said needle, said stepping mechanism interacting with said actuating element.

35. The dispenser according to claim 34, wherein said stepping mechanism is an integral part of said actuating element.

36. The dispenser according to claim 22, wherein, once a cavity has been emptied, said carrier accommodating the blister is advanced by one step during a course of a return displacement of said actuating element that is to be carried out manually.

37. The dispenser according to claim 22, which further comprises a mouthpiece closure cap, which is connected in a controlling manner to the annular blister carrier driven by a stepping mechanism.

38. The dispenser according to claim 36, which further comprises a blocking lug disposed in a rotationally fixed manner on said actuating element and disposed for interaction with said mouthpiece closure cap.

39. The dispenser according to claim 38, wherein said mouthpiece closure cap is formed with a recess which is open at an edge, for said blocking lug to enter in a ready position of the dispenser.

40. The dispenser according to claim 39, wherein said mouthpiece closure cap has a blocking shoulder at a spacing from said recess which interacts with the blocking lug in an unready position.

41. The dispenser according to claim 22, wherein said housing has a swirl chamber formed therein and, before the suction air stream leaves said mouthpiece, the suction air stream transporting the substance passes through said swirl chamber.

42. The dispenser according to claim 22 configured as a medicament dispenser.

43. A dispenser for dispensing pulverulent substances, comprising:

a dispenser housing having a mouthpiece;

a circular blister pack having a center and being movably disposed in said dispenser housing, said blister pack having a plurality of domes disposed radially about said center and forming dome-shaped cavities on a base layer, said domes having a lateral wall and being disposed for moving said dome-shaped cavities, by stepwise movement within said dispenser housing, into an emptying position;

a needle movably disposed in said dispenser housing for opening said dome-shaped cavities in said emptying position for emptying by a suction air stream leading to said mouthpiece, said needle passing through said lateral wall of said dome in a radial direction outward from the center of said circular blister pack to pierce a punched hole into the lateral wall, said punched hole being open after retraction of said needle, lying in a path of the suction air stream channel leading to said mouthpiece said needle having elastically yielding spring arms formed thereon at an end thereof remote from a tip of said needle; and means for conducting the suction air stream emptying the cavity through said dispenser housing with a deflection of 180° before entering the cavity.

44. The dispenser according to claim 43, wherein all of domes penetrate into respective individual accommodating holes in a carrier and close off a transverse channel of said carrier, prior to piercing by said needle.

45. The dispenser according to claim 43, wherein said base layer is an annular base layer.

46. The dispenser according to claim 43, wherein said needle pierces said later walls of said dome along a straight line extending substantially along a diameter line.

47. The dispenser according to claim 43, wherein a diameter of said needle corresponds to one sixth to one third of a diameter of said dome.

48. The dispenser according to claim 43, wherein said needle is disposed to run through said dome wall near a base layer of said cavities.

49. The dispenser according to claim 43, wherein said needle passes through said dome while building up a spring force and wherein, after passing through said dome, said needle returns automatically, triggered by a release of the spring force.

50. The dispenser according to claim 43, wherein a triggering of the needle return displacement takes place automatically.

51. The dispenser according to claim 43, which comprises a drag part for moving said needle into a piercing position.

52. The dispenser according to claim 51, which comprises an actuating element coupled to a user-accessible handle, for displacing said drag part in a triggerable manner.

53. The dispenser according to claim 43, wherein said needle is formed in one piece with said spring arms.

54. The dispenser according to claim 43, wherein said needle is a solid plastic, injection-molded component formed with said spring arms.

55. The dispenser according to claim 43, which comprises a stepping mechanism, for moving said dome-shaped cavities step by step into said emptying position, and a user-actuated actuating element for piercing said dome-shaped cavities with said needle, said stepping mechanism interacting with said actuating element.

56. The dispenser according to claim 55, wherein said stepping mechanism is an integral part of said actuating element.

57. The dispenser according to claim 43, wherein, once a cavity has been emptied, said carrier accommodating the blister is advanced by one step during a course of a return displacement of said actuating element that is to be carried out manually.

58. The dispenser according to claim 43, which further comprises a mouthpiece closure cap, which is connected in a controlling manner to the annular blister carrier driven by a stepping mechanism.

59. The dispenser according to claim 58, which further comprises a blocking lug disposed in a rotationally fixed manner on said actuating element and disposed for interaction with said mouthpiece closure cap.

60. The dispenser according to claim 59, wherein said mouthpiece closure cap is formed with a recess which is open at an edge, for said blocking lug to enter in a ready position of the dispenser.

61. The dispenser according to claim 60, wherein said mouthpiece closure cap has a blocking shoulder at a spacing from said recess which interacts with the blocking lug in an unready position.

62. The dispenser according to claim 43, wherein said housing has a swirl chamber formed therein and, before the suction air stream leaves said mouthpiece, the suction air stream transporting the substance passes through said swirl chamber.

63. The dispenser according to claim 43 configured as a medicament dispenser.

* * * * *